US012788783B2

(12) United States Patent
Kim

(10) Patent No.: US 12,788,783 B2
(45) Date of Patent: Nov. 10, 2026

(54) METHOD FOR DIRECT REPROGRAMMING FROM SOMATIC CELLS INTO PANCREATIC BETA CELLS BY USING MICRORNA, AND DIFFERENTIATION COMPOSITION

(71) Applicant: Research & Business Foundation Sungkyunkwan University, Suwon-si (KR)

(72) Inventor: Kyeong Kyu Kim, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 894 days.

(21) Appl. No.: 18/246,663

(22) PCT Filed: Sep. 23, 2021

(86) PCT No.: PCT/KR2021/012922
§ 371 (c)(1),
(2) Date: Mar. 24, 2023

(87) PCT Pub. No.: WO2022/065859
PCT Pub. Date: Mar. 31, 2022

(65) Prior Publication Data

US 2023/0364153 A1 Nov. 16, 2023

(30) Foreign Application Priority Data

Sep. 24, 2020 (KR) ........................ 10-2020-0123558
Aug. 4, 2021 (KR) ........................ 10-2021-0102649

(51) Int. Cl.
*A61K 35/39* (2015.01)
*A61K 45/06* (2006.01)
*C12N 5/071* (2010.01)
*C12N 15/113* (2010.01)

(52) U.S. Cl.
CPC .............. *A61K 35/39* (2013.01); *A61K 45/06* (2013.01); *C12N 5/0676* (2013.01); *C12N 15/113* (2013.01); *C12N 2310/141* (2013.01); *C12N 2500/38* (2013.01); *C12N 2501/16* (2013.01); *C12N 2501/41* (2013.01); *C12N 2501/65* (2013.01); *C12N 2501/727* (2013.01); *C12N 2506/1307* (2013.01); *C12N 2506/22* (2013.01)

(58) Field of Classification Search
CPC ........ A61K 35/39; A61K 45/06; A61K 31/00; A61K 31/7105; C12N 5/0676; C12N 15/113; C12N 2310/141; C12N 2500/38; C12N 2501/16; C12N 2501/41; C12N 2501/65; C12N 2501/727; C12N 2506/1307; C12N 2506/22
See application file for complete search history.

(56) References Cited

FOREIGN PATENT DOCUMENTS

| | | | | |
|---|---|---|---|---|
| KR | 10-2012-0095257 A | | 8/2012 | |
| KR | 10-1524079 B1 | | 6/2015 | |
| WO | WO-2018125019 A2 | * | 7/2018 | ............. A61K 45/06 |

OTHER PUBLICATIONS

Mandal et al., 2020. Exosome-mediated differentiation of mouse embryonic fibroblasts and exocrine cells into β-like cells and the identification of key miRNAs for differentiation. Biomedicines, 8(11), p. 485. (Year: 2020).*
Leng et al. "Glycogen synthase kinase 3b mediates high glucose-induced ubiquitination and proteasome degradation of insulin receptor substrate" *The Journal of endocrinology* vol. 206 No. 2, Aug. 2010 (pp. 1-12).
Chen et al. "miR-709 inhibits 3T3-L1 cell differentiation by targeting GSK3β of Wnt/β-catenin signaling" *Cellular signalling* vol. 26 No. 11, Jul. 16, 2014 (pp. 2583-2589).

* cited by examiner

*Primary Examiner* — Jeremy C Flinders
*Assistant Examiner* — Masudur Rahman
(74) *Attorney, Agent, or Firm* — NSIP Law

(57) ABSTRACT

The present invention relates to a method for direct reprogramming from somatic cells into pancreatic beta cells by using microRNA and small-molecule materials. The inventors of the present invention confirmed that, as a result of having attempted direct reprogramming upon co-treatment of microRNA and small-molecules (e.g., various differentiation-inducing materials), the expression level of PDX1 remarkably increased in pancreatic beta cells, and, when pancreatic beta-like cells were induced using such a method, direct reprogramming was performed with very high yield. In addition, since autologous cells are used, the present invention has the advantages of no occurrence of immune rejection responses and a low possibility of developing cancer, and thus is expected to be effectively used in the development of safer cellular therapeutic agents. In addition, pancreatic beta cells produced by the present invention are expected to be effectively used in a cellular composition for preventing, treating and ameliorating diabetes or pancreatic cancer.

13 Claims, 14 Drawing Sheets

Specification includes a Sequence Listing.

Our final protocol

| | miR-127 | miR-709 |
|---|---|---|
| **Combination-1** | 100nM | 100nM |
| **Combination-2** | 133M | 66nM |
| **Combination-3** | 66nM | 133nM |

| | miR-127 | miR-709 | miR-19b |
|---|---|---|---|
| **Combination-1** | 66nM | 66nM | 66nM |
| **Combination-2** | 160nM | 20nM | 20nM |
| **Combination-3** | 20nM | 160nM | 20nM |
| **Combination-4** | 20nM | 20nM | 160nM |

Control mimic-200nM-266-6

Control mimic-200nM-266-6

| Legend | SB203580 | Nicotinamide | Exendin-4 | Bay K-8644 | MiRNA 127 |
|---|---|---|---|---|---|
| A1 | YES | YES | YES | NO | YES |
| B1 | YES | YES | NO | YES | YES |
| C1 | YES | NO | YES | YES | YES |
| D1 | NO | YES | YES | YES | YES |
| E1 | YES | YES | YES | YES | YES |

SEQUENCE LISTING

```
<160> NUMBER OF SEQ ID NOS: 5

<210> SEQ ID NO 1
<211> LENGTH: 22
<212> TYPE: RNA
<213> ORGANISM: Artificial Sequence
<220> FEATURE:
<223> OTHER INFORMATION: miR-127-5p

<400> SEQUENCE: 1

cugaagcuca gagggcucug au                                              22
```

-continued

```
<210> SEQ ID NO 2
<211> LENGTH: 19
<212> TYPE: RNA
<213> ORGANISM: Artificial Sequence
<220> FEATURE:
<223> OTHER INFORMATION: miR-709

<400> SEQUENCE: 2

ggaggcagag gcaggagga                                          19


<210> SEQ ID NO 3
<211> LENGTH: 70
<212> TYPE: RNA
<213> ORGANISM: Artificial Sequence
<220> FEATURE:
<223> OTHER INFORMATION: miR-127 MI0000154 precursor

<400> SEQUENCE: 3

ccagccugcu gaagcucaga gggcucugau ucagaaagau caucggaucc gucugagcuu     60

ggcuggucgg                                                            70


<210> SEQ ID NO 4
<211> LENGTH: 88
<212> TYPE: RNA
<213> ORGANISM: Artificial Sequence
<220> FEATURE:
<223> OTHER INFORMATION: miR-709 MI0004693 precursor

<400> SEQUENCE: 4

ugucccguuu cucugcuucu acucagaagu gcucugagca uagaacuguc cuguuugagc     60

agcacugggg aggcagaggc aggaggau                                        88


<210> SEQ ID NO 5
<211> LENGTH: 23
<212> TYPE: RNA
<213> ORGANISM: Artificial Sequence
<220> FEATURE:
<223> OTHER INFORMATION: miR-19b

<400> SEQUENCE: 5

ugugcaaauc caugcaaaac uga                                             23
```

METHOD FOR DIRECT REPROGRAMMING FROM SOMATIC CELLS INTO PANCREATIC BETA CELLS BY USING MICRORNA, AND DIFFERENTIATION COMPOSITION

CROSS REFERENCE TO RELATED APPLICATIONS

This application is a U.S. National Stage Application of International Application No. PCT/KR2021/012922, filed on Sep. 23, 2021, which claims the benefit under 35 USC 119 (a) and 365 (b) of Korean Patent Application No. 10-2020-0123558, filed on Sep. 24, 2020 and Korean Patent Application No. 10-2021-0102649, filed on Aug. 4, 2021 in the Korean Intellectual Property Office, the entire disclosure of which is incorporated herein by reference for all purposes.

TECHNICAL FIELD

The present disclosure relates to a method for direct reprogramming from somatic cells into pancreatic beta cells and a differentiation composition, and more specifically to a composition for inducing direct reprogramming of somatic cells into pancreatic beta cells, containing one or more selected from the group consisting of micro RNAs (miRNAs) (miR-127 and miR-709) as an active ingredient, a method for direct reprogramming of pancreatic beta cells using the composition, etc.

This application claims priority based on Korean Patent Application No. 10-2020-0123558, filed on Sep. 24, 2020, and Korean Patent Application No. 10-2021-0102649, filed on Aug. 4, 2021, and all contents disclosed in the specification and drawings of the application are incorporated herein by reference.

BACKGROUND ART

In diabetes, glucose toxicity causes apoptosis of β-cells and affects various organ systems, including the pancreas. However, the underlying mechanism has not been fully elucidated. Disorder of β-cells and impaired insulin production are typical features of diabetes, but the exact molecular mechanism of glucose toxicity that causes β-cell apoptosis is still unknown despite the rapid spread of diabetes.

In particular, in diseases such as type 1 diabetes mellitus and pancreatic cancer, malfunction is induced by damage or loss of beta cells; therefore, the method of transplantation of pancreatic beta cells is the only treatment.

Recent advances in stem cell research have not only reduced issues relating to time and effectiveness in the process of direct reprogramming (redifferentiation or reprogramming) of somatic cells into various lineages without undergoing intermediate differentiation, but also opened a new path for autologous transplantation. However, pancreatic beta cells derived from induced pluripotent stem cells (iPSCs) may have immune rejection reactions because cells from other people are used; additionally, there may be a problem in stability due to the cancer-causing potential of stem cells.

Accordingly, a method for direct reprogramming that converts one's own somatic cells into pancreatic beta cells has been in the spotlight. The methods for converting somatic cells into pancreatic beta cells include a method of forcibly expressing the marker gene of beta cells and a method of using a small molecule; however, the method of introducing a foreign gene had a problem in that it affects the genome and thus may cause cancer and the method of using a small molecule had a problem in that it reduces the conversion efficiency into pancreatic beta cells.

In addition, the conventional method had a disadvantage in that the period required for the conversion into pancreatic beta cells was too long, being 27 days or more; therefore, there was a need for shortening of the period (*Cell Stem Cell.* 2014 Feb. 6; 14(2): 228-36. doi:10.1016/j.stem.2014.01.006).

In order to overcome such problems, the present inventors have developed a technology for effectively converting somatic cells into pancreatic beta cells in a short time by treating somatic cells with microRNA alone or together with a small molecule.

DISCLOSURE

Technical Problem

The present disclosure has been devised to solve the problems in the prior art as described above, and the present inventors have made many efforts to find a method for directly changing somatic cells into pancreatic beta cells; as a result, they have confirmed that the microRNA of the present disclosure alone or a composition containing microRNA and a histone methyltransferase inhibitor, retinoic acid agonist, ALK-5 kinase inhibitor, hedgehog inhibitor, MAPK inhibitor, calcium channel agonist, GLP receptor agonist and a supplement can be treated to induce the conversion of somatic cells into pancreatic beta cells, thereby completing the present disclosure.

Accordingly, it is an object of the present disclosure to provide a composition for inducing direct reprogramming of somatic cells into pancreatic beta cells, which contains one or more miRNA selected from the group consisting of miR-127 and miR-709.

Another object of the present disclosure is to provide a method for direct reprogramming from somatic cells to pancreatic beta cells, which includes culturing somatic cells in the presence of a composition that contains a MAPK inhibitor, a calcium channel agonist, a GLP receptor agonist, and a supplement, and one or more miRNA selected from the group consisting of miR-127 and miR-709.

Still another object of the present disclosure is to provide a pharmaceutical composition for preventing or treating diabetes or pancreatic cancer, which contains one or more miRNA selected from the group consisting of miR-127 and miR-709 as an active ingredient.

Still another object of the present disclosure is to provide a method for preparing a cellular therapeutic agent for treating diabetes or pancreatic cancer, which includes mixing pancreatic beta cells, whose direct reprogramming was induced by the method described above, with one or more selected from the group consisting of pharmaceutically acceptable carriers and excipients.

Still another object of the present disclosure is to provide a method for preventing or treating diabetes or pancreatic cancer, which includes delivering a composition containing one or more miRNA selected from the group consisting of miR-127 and miR-709 as an active ingredient into the living body to induce direct reprogramming of somatic cells into beta cells in vivo.

However, the technical problem to be achieved by the present disclosure is not limited to the problems mentioned above, and other problems not mentioned above will be clearly understood by those skilled in the art from the description provided herein below.

Technical Solution

In order to achieve the above objects, the present disclosure provides a composition for inducing direct reprogramming of somatic cells into pancreatic beta cells, containing micro RNA or a small molecule as an active ingredient.

In addition, the present disclosure provides a composition for inducing direct reprogramming of somatic cells into pancreatic beta cells, which contains one or more miRNA selected from the group consisting of miR-127 and miR-709.

In one embodiment of the present disclosure, the somatic cell may be one or more selected from the group consisting of a fibroblast, a pancreatic ductal cell, and an exocrine cell, but is not limited thereto.

In another embodiment of the present disclosure, the composition may further include miR-19b, but is not limited thereto.

In still another embodiment of the present disclosure, the composition may further include one or more small molecule selected from the group consisting of a histone methyltransferase inhibitor, a retinoic acid agonist, an ALK-5 kinase inhibitor, a hedgehog inhibitor, a MAPK inhibitor, a calcium channel agonist, a GLP receptor agonist, and a supplement, but is not limited thereto.

In still another embodiment of the present disclosure, the histone methyltransferase inhibitor may be one or more selected from the group consisting of BIX01294 (2-(Hexahydro-4-methyl-1H-1,4-diazepin-1-yl)-6,7-dimethoxy-N-[1-(phenylmethyl)-4-piperidinyl]-4-quinazolinamine), decitabine (5-aza-2'-deoxycytidine; DAC), zebularine, 3'-deazaneplanocin A hydrochloride, lomeguatrib, and chaetocin (2,2',3S,3'S,5aR,5'aR,6,6'-octahydro-3,3'-bis(hydroxymethyl)-2,2'-dimethyl-[10bR,10'bR(11aS,11'aS)-bi-3,11a-epidithio-11aH-pyrazino[1',2':1,5]pyrrolo[2,3-b]indole]-1,1',4,4'-tetrone), but is not limited thereto.

In still another embodiment of the present disclosure, the supplement is one or more selected from the group consisting of 2-phospho-L-ascorbic acid, B27, laminin, nicotinamide, and N2, but is not limited thereto.

In still another embodiment of the present disclosure, the retinoic acid agonist is one or more selected from the group consisting of TTNPB, phytic acid, and retinoic acid, but is not limited thereto.

In still another embodiment of the present disclosure, the hedgehog inhibitor is one or more selected from the group consisting of cyclopamine, mifepristone, GDC-0449 (vismodegib), XL139 (BMS-833923), IPI926, IPI609 (IPI269609), LDE225, jervine, GANT61, pumorphamine, SAG, SANT-2, tomatidine, SANT74, SANT75, zerumbone, and derivatives thereof, but is not limited thereto.

In still another embodiment of the present disclosure, the MAPK inhibitor is one or more selected from the group consisting of 1-pyridinyl-2-phenylazole, SB 203580, SKF 86002, SKF 86096, SKF 104351, 1-aryl-2-pyridinyl/pyrimidinyl heterocycles, SB 242235, RO-32001195, SX-011, and BIRB-796, but is not limited thereto.

In still another embodiment of the present disclosure, the ALK-5 kinase inhibitor is one or more selected from the group consisting of RepSox (1,5-naphthyridine, 2-[3-(6-methyl-2-pyridinyl)-1H-pyrazol-4-yl]); SB525334 (6-(2-tert-butyl-4-(6-methylpyridin-2-yl)-1H-imidazol-5-yl)quinoxaline); GW788388 (4-(4-(3)-(pyridin-2-yl)-1H-pyrazol-4-yl)pyridin-2-yl)-N-(tetrahydro-2H-pyran-4-yl) benzamide); SD-208 (2-(5-chloro-2-fluorophenyl)-N-(pyridin-4-yl)pteridin-4-amine); Galunisertib (LY2157299, 4-(2-(6-methylpyridin-2-yl)-5,6-dihydro-4H-pyrrolo[1,2-b] pyrazol-3-yl)quinoline-6-carboxamide); EW-7197 (N-(2-fluorophenyl)-5-(6-methyl-2-pyridinyl)-4-[1,2,4]triazolo[1,5-a]pyridin-6-yl-1H-imidazole-2-methanamine); LY2109761 (7-(2-morpholinoethoxy)-4-(2-(pyridin-2-yl)-5,6-dihydro-4H-pyrrolo[1,2-b]pyrazol-3-yl)quinoline); SB505124 (2-(4-(benzo[d][1,3]dioxol-5-yl)-2-tert-butyl-1H-imidazol-5-yl)-6-methylpyridine); LY364947 (quinoline, 4-[3-(2-pyridinyl)-1H-pyrazol-4-yl]); SB431542 (4-(4-(benzo[d][1,3]dioxol-5-yl)-5-(pyridin-2-yl)-1H-imidazol-2-yl)benzamide); K02288 (3)-[(6-amino-5-(3),4,5-trimethoxyphenyl)-3-pyridinyl]phenol]; and LDN-212854 (quinoline, 5-[6-[4-(1-piperazinyl)phenyl]pyrazolo[1,5-a] pyrimidin-3-yl]), but is not limited thereto.

In still another embodiment of the present disclosure, the calcium channel agonist is one or more selected from the group consisting of Bay K-8644, FPL 64179, and CGP28392, but is not limited thereto.

In still another embodiment of the present disclosure, the GLP receptor agonist is one or more selected from the group consisting of dulaglutide, exenatide, semaglutide, liraglutide, lixisenatide, and albiglutide, but is not limited thereto.

In addition, the present disclosure provides a method for direct reprogramming from somatic cells to pancreatic beta cells, which includes culturing somatic cells in the presence of a composition containing a MAPK inhibitor, a calcium channel agonist, a GLP receptor agonist, and a supplement, and one or more miRNA selected from the group consisting of miR-127 and miR-709, but the method is not limited thereto.

In an embodiment of the present disclosure, the method may include or consist of the stages of (1) inducing somatic cells into pancreatic endoderm cells; (2) inducing pancreatic endoderm cells into pancreatic progenitor cells; and (3) inducing the pancreatic progenitor cells into pancreatic beta cells, but the method is not limited thereto.

In another embodiment of the present disclosure, the method may include or consist of (3) inducing pancreatic progenitor cells into pancreatic beta cells, but the method is not limited thereto.

In still another embodiment of the present disclosure, while when the somatic cells of the method are fibroblasts, differentiation is required through three stages, when the somatic cells are pancreatic duct cells and exocrine cells having the properties of pancreatic progenitor cells, somatic cells can be directly reprogrammed into pancreatic beta cells in the presence of the composition.

In still another embodiment of the present disclosure, the direct reprogramming method may include the following stages, but is not limited thereto:

(1) inducing somatic cells into pancreatic endoderm cells in the presence of a composition containing a histone methyltransferase inhibitor, activin A, and a supplement, and one or more miRNA selected from the group consisting of miR-127 and miR-709;

(2) inducing the pancreatic endoderm cells into pancreatic progenitor cells in the presence of a composition containing a retinoic acid agonist, an ALK-5 kinase inhibitor, a hedgehog inhibitor and a supplement, and one or more miRNA selected from the group consisting of miR-127 and miR-709; and (3) culturing the somatic cells in the presence of a composition containing a MAPK inhibitor, a calcium channel agonist, a GLP receptor agonist and a supplement, and one or more miRNA selected from the group consisting of miR-127 and miR-709.

In addition, the present disclosure provides a pharmaceutical composition for preventing or treating diabetes or pancreatic cancer, which contains one or more miRNA selected from the group consisting of miR-127 and miR-709 as an active ingredient.

In an embodiment of the present disclosure, the diabetes may be selected from the group consisting of type 1 diabetes, type 2 diabetes, and gestational diabetes, but is not limited thereto.

In addition, the present disclosure provides a method for preparing a cellular therapeutic agent for treating diabetes or pancreatic cancer, which includes mixing the pancreatic beta cells induced by the direct reprogramming method described above with one or more selected from the group consisting of pharmaceutically acceptable carriers and excipients.

In addition, the present disclosure provides a cellular therapeutic agent for treating diabetes or pancreatic cancer containing pancreatic beta cells, whose direct reprogramming was induced by the method described above, as an active ingredient.

In addition, the present disclosure provides a method for preventing or treating diabetes or pancreatic cancer, which includes delivering a composition containing one or more miRNA selected from the group consisting of miR-127 and miR-709 into the living body to induce direct reprogramming of somatic cells into beta cells in vivo.

In addition, the present disclosure provides a method for preventing or treating diabetes or pancreatic cancer, which includes administering a pharmaceutical composition containing one or more miRNA selected from the group consisting of miR-127 and miR-709; or pancreatic beta cells, whose direct reprogramming was induced by the method described above, as an active ingredient to a subject in need thereof.

In addition, the present disclosure provides a use of a pharmaceutical composition for preventing or treating diabetes or pancreatic cancer, which contains one or more miRNA selected from the group consisting of miR-127 and miR-709; or pancreatic beta cells, whose direct reprogramming was induced by the method described above, as an active ingredient.

In addition, the present disclosure provides a use of one or more miRNA selected from the group consisting of miR-127 and miR-709; or pancreatic beta cells, whose direct reprogramming was induced by the method described above, in preparation of a therapeutic agent for diabetes or pancreatic cancer.

In addition, the present disclosure provides a use of a composition which contains one or more miRNA selected from the group consisting of miR-127 and miR-709 to induce direct reprogramming of somatic cells into pancreatic beta cells.

In addition, the present disclosure provides a kit for inducing direct reprogramming of somatic cells into pancreatic beta cells, which includes a composition containing one or more miRNA selected from the group consisting of miR-127 and miR-709.

Advantageous Effects

The present disclosure relates to a method for direct reprogramming from somatic cells into pancreatic beta cells by using microRNA and small-molecule materials. The inventors of the present disclosure confirmed that, as a result of having attempted direct reprogramming upon co-treatment of microRNA and small-molecule materials such as various differentiation-inducing materials, the expression level of PDX1 remarkably increased in pancreatic beta cells, and, when pancreatic beta-like cells were induced using such a method, direct reprogramming was performed with very high yield. In addition, when the converted pancreatic beta cells are transplanted to patients with diabetes or pancreatic cancer, since autologous cells are used, the present disclosure has the advantages of no occurrence of immune rejection responses and a low possibility of developing cancer, and thus is expected to be effectively used in the development of safer cellular therapeutic agents. In addition, pancreatic beta cells produced by the present disclosure are expected to be effectively used in a cellular composition for preventing, treating, and ameliorating diabetes or pancreatic cancer.

DESCRIPTION OF DRAWINGS

FIG. 2*a* shows the results of comparison of expression of Pdx1 gene in stage-1 cells after treatment with various types of miRNAs.

FIG. 2*b* shows the effect of inducing Pdx1 expression according to the combination of miR-127 and miR-709 at different concentrations in stage-1 cells.

FIG. 2*c* shows Ngn3 transcript levels in stage-1 cells after transfection with miR-127 and miR-709 using Combination-3.

FIG. 2*d* shows the results of confirming the pancreatic gene expression profile of the stage-2 cells transfected with miR-127 and miR-709 (Combination-3) by qRT-PCR.

FIG. 2*e* shows the results of confirming the pancreatic β-cell marker by qRT-PCR in stage-3 cells transfected with miR-127 and miR-709 (Combination-3).

FIG. 3*a* shows the results of transfection of the 5' FAM-labeled control mimic to optimize transfection efficiency in fibroblasts. A brightfield microscopy image (left) and a fluorescence microscopy image (right) are shown after transfection in a Stage 1 medium for 48 hours. Scale bar=100 μm.

FIG. 3*b* shows the effect of inducing expression of Pdx1 according to various concentration combinations of miR-127, miR-709, and miR-19b in Stage 1 medium using qRT-PCR analysis. $*P<0.05$, $P<0.01$, $*P<0.001$. Statistical significance was determined by a two-way, paired Student's t-test. Data shown represent mean f SEM from three independent experiments.

FIG. 3*c* shows the morphological changes in MEFs according to each of the different combinations of treatments in stage-1 differentiation (after 48 hours) represented by bright field microscopy images. Scale bar=100 μm.

FIG. 4*a* shows the results of optimization of transfection of 266-6 cells in Stage 3 medium, and shows a bright field microscopy image (left) and a fluorescence microscopy image (right) after transfection in Stage 3 medium for 48 hours.

FIG. 4*b* shows the transcription levels of Pdx1, Ngn3, Insulin-1, Insulin-2, and Elastase after transfecting 266-6 cells with miR-127+miR-709 (Combination-3). Combination-3 reduced the expression of Elastase, which is an acinar cell marker. *$P<0.05$ and **$P<0.01$. Statistical significance was determined by a two-way, paired Student's t-test. Data shown represent mean±SEM from three independent experiments.

BEST MODE FOR CARRYING OUT THE INVENTION

Figure 1A:
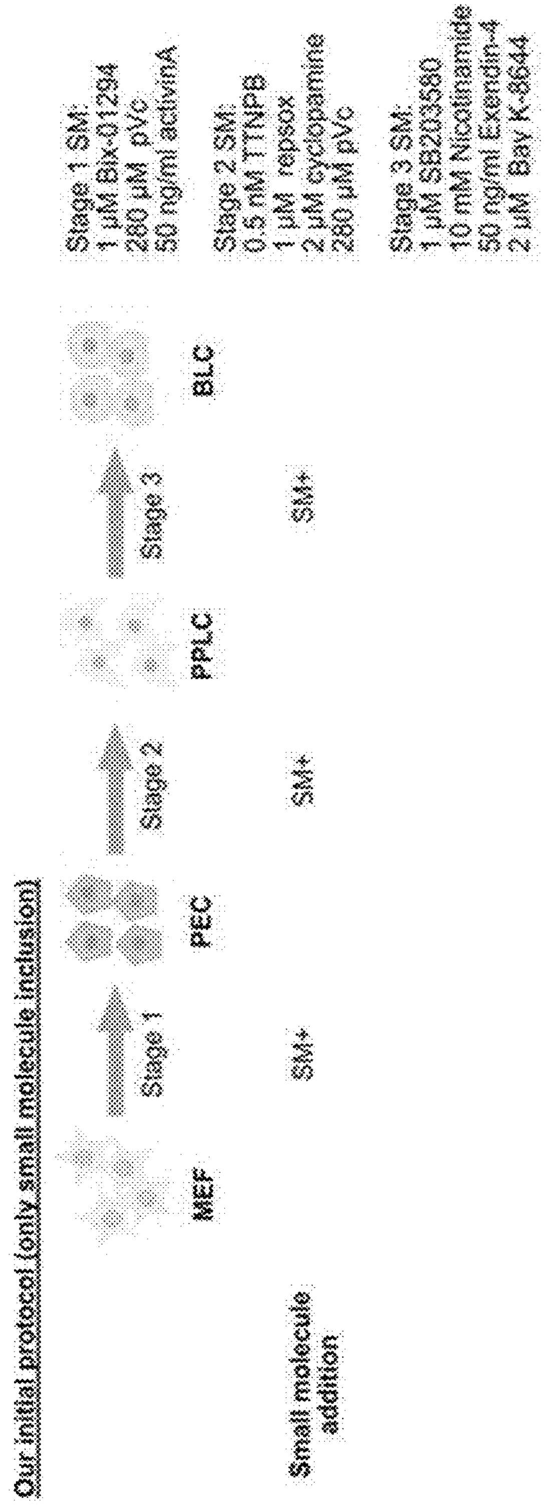
FIG. 1*a* shows a diagram illustrating a method for converting somatic cells into beta cells using a small molecule.

The present inventors have confirmed that direct reprogramming into pancreatic beta cells was remarkably improved when micro RNA and a small molecule were used in combination, compared to when only micro RNA was used alone, when a small molecule was used alone, and when the control group that was untreated. Accordingly, the present disclosure provides a composition for inducing direct reprogramming of somatic cells into pancreatic beta cells, which contains a specific microRNA as an active ingredient, and more specifically, relates to a composition for inducing direct reprogramming of somatic cells into pancreatic beta cells, which contains one or more selected from the group consisting of miR-127 and miR-709.

Hereinafter, the present disclosure will be described in detail.

In the present disclosure, "micro RNA (miRNA, microRNA)" is a small noncoding RNA of about 22 nucleotides in length that serves as a negative regulator of gene expression by inhibiting mRNA translation or promoting mRNA degradation.

In the present disclosure, "miR-127" may include or consist of a nucleotide sequence represented by SEQ ID NO: 1, but is not limited thereto.

In the present disclosure, "miR-709" may include or consist of a nucleotide sequence represented by SEQ ID NO: 2, but is not limited thereto.

In the present disclosure, "miR-19b" may include or consist of a nucleotide sequence represented by SEQ ID NO: 5, but is not limited thereto.

In the present disclosure, miR-127 and miR-709 may be included at a molar concentration (M) ratio of 0.1 to 10:1, 1 to 3:1, 1:1 to 3, or 1:1, but is not limited thereto.

In the present disclosure, miR-127, miR-709, and miR-19b may be included at a molar concentration (M) ratio of 0.1 to 10:0.1 to 10:1, at a molar concentration (M) ratio of 1 to 3:1 to 3:1, or at a molar concentration (M) ratio of 1:1:1, but is not limited thereto.

In inducing the pancreatic beta cells of the present disclosure, the type of the starting somatic cells (parent cells) is not particularly limited, and any somatic cells may be used. For example, in addition to the somatic cells of the embryonic period, mature somatic cells may also be used. When induced pancreatic beta cells are used for treatment of a disease, it is preferable to use somatic cells isolated from a patient, for example, somatic cells involved in disease, somatic cells involved in disease treatment, etc. may be used. Meanwhile, the somatic cell of the present disclosure may be a human pancreas-derived cell, but is not limited thereto. The somatic cells may be fibroblasts, pancreatic duct cells, or exocrine cells, and in the present disclosure, the somatic cells include all of those derived from humans and animals such as mice, horses, sheep, pigs, goats, camels, antelopes, and dogs.

In the present disclosure, the term "pancreatic beta cells", which are cells constituting the islets of Langerhans in the pancreas and are cells that produce and secrete insulin, may be used interchangeably with "pancreatic beta-cell-like cells". If there is a problem with the beta cells of the pancreas, it may cause a problem in the production of insulin and thus may lead to diabetes. Therefore, these cells can be used for the treatment of diabetes caused by a problem in the secretion of pancreatic insulin.

As used herein, the term "pancreatic progenitor cell" refers to an endoderm cell that can be differentiated into a pancreatic endocrine cell and a pancreatic exocrine cell, and in the present disclosure, the pancreatic progenitor cell may be induced to be differentiated into a pancreatic beta cell.

In an embodiment of the present disclosure, it was confirmed that the pancreatic beta cells, which were directly reprogrammed by treating somatic cells with microRNA and a small molecule, show high expression of pancreas-specific gene markers PDX1, Ngn3, Ins-1, and Ins-2.

In the present disclosure, the composition may further include miR-19b, but is not limited thereto.

In the present disclosure, the composition may further include one or more small molecule selected from the group consisting of a histone methyltransferase inhibitor, a retinoic acid agonist, an ALK-5 kinase inhibitor, a hedgehog inhibitor, a MAPK inhibitor, a calcium channel agonist, a GLP receptor agonist, and a supplement, but is not limited thereto.

In the present disclosure, when the composition includes a histone methyltransferase inhibitor, the composition may be for inducing differentiation of somatic cells into pancreatic endoderm cells, but is not limited thereto.

In the present disclosure, when the composition includes a retinoic acid agonist, an ALK-5 kinase inhibitor, and a hedgehog inhibitor, the composition may be for inducing differentiation of somatic cells or pancreatic endoderm cells into pancreatic progenitor cells, but is not limited thereto.

In the present disclosure, when the composition includes a MAPK inhibitor, a calcium channel agonist, and a GLP receptor agonist, the composition may be for inducing the maturation of pancreatic beta cells, but is not limited thereto.

As used herein, the term "maturation" refers to conversion of the cells induced into pancreatic beta cells into beta cells having more perfect activity.

As used herein, the term "histone methyltransferase inhibitor" refers to an enzyme that catalyzes the transfer of a methyl group from a donor to a recipient. The histone methyltransferase inhibitor that can be used herein may be selected from the group consisting of BIX01294 (2-(hexahydro-4-methyl-1H-1,4-diazepin-1-yl)-6,7-dimethoxy-N-[1-(phenylmethyl)-4-piperidinyl]-4-quinazolinamine), decitabine (5-aza-2'-deoxycytidine, DAC), zebularine, 3'-deazaneplanocin A hydrochloride (3'-deazaneplanocin A) hydrochloride, lomeguatrib, and chaetocin (2,2',3S,3'S,5aR,5'aR,6,6'-octahydro-3,3'-bis(hydroxymethyl)-2,2'-dimethyl-[10bR,10'bR(11aS,11'aS)-bi-3,11a-epidithio-11aH-pyrazino[1',2':1,5]pyrrolo[2,3-b]indole]-1,1',4,4'-tetrone), but is not limited thereto.

In the present disclosure, the term "retinoic acid agonist" may preferably be a retinoic acid receptor agonist (RAR agonist), and may be one or more selected from the group consisting of 4-[(E)-2-(5,6,7),8-tetrahydro-5,5,8,8-tetramethyl-2-naphthalenyl)-1-propenyl]benzoic acid (TTNPB, arotinoid acid), phytanic acid, and retinoic acid (RA), but is not limited thereto. The RAR receptor activates transcription by binding to a DNA sequence element known as a RAR response element (RARE) in the form of a heterodimer with a retinoid X receptor (known as RXR). The prior art technology includes a number of compounds that are RAR type receptor ligands. Among the prior art documents, examples that can be mentioned include U.S. Pat. No. 6,150,413 that discloses triaromatic compounds, U.S. Pat. No. 6,214,878 that discloses stilbene compounds, or U.S. Pat. No. 6,218,128 that discloses a group of bicyclic or tricyclic molecules. The medium of the present disclosure may contain the retinoic acid agonist in the range of 0.01 nM to 30 nM, 0.01 nM to 20 nM, 0.01 nM to 10 nM, 0.1 nM to 30 nM, 0.01 nM to 20 nM, 0.01 nM to 10 nM, 0.1 nM to 8 nM, 0.1 nM to 6 nM, 0.1 nM to 3 nM, 0.1 nM to 2 nM, 0.1 nM to 1 nM, 0.1 nM to 0.8 nM, 0.1 nM to 0.7 nM, 0.3 nM to 1 nM, 0.3 nM to 0.7 nM, or about 0.5 nM, but the concentration of the medium is not limited thereto.

In the present disclosure, "ALK-5 kinase inhibitor" refers to a material that binds to the TGF-β type I receptor and thereby interferes with the normal signaling process of TGF-β I. TGF-β type I (transforming growth factor-β type I) is a multifunctional peptide that has various actions on cell proliferation, differentiation, and various types of cells, and such multifunctionality plays a crucial role in the growth and differentiation of various tissues such as adipocyte formation, myocyte formation, osteocyte formation, and epithelial cell differentiation. The ALK-5 kinase inhibitor (a TGF-β type I receptor inhibitor) may include RepSox (1,5-naphthyridine, 2-[3-(6-methyl-2-pyridinyl)-1H-pyrazol-4-yl]); SB525334 (6-(2-tert-butyl-4-(6-methylpyridin-2-yl)-1H-imidazol-5-yl)quinoxaline); GW788388 (4-(4-(3)-(pyridin-2-yl)-1H-pyrazol-4-yl)pyridin-2-yl)-N-(tetrahydro-2H-pyran-4-yl)benzamide); SD-208 (2-(5-chloro-2-fluorophenyl)-N-(pyridin-4-yl)pteridin-4-amine); galunisertib (LY2157299, 4-(2-(6-methylpyridin-2-yl)-5,6-dihydro-4H-pyrrolo[1,2-b]pyrazol-3-yl)quinoline-6-carboxamide); EW-7197 (N-(2-fluorophenyl)-5-(6-methyl-2-pyridinyl)-4-[1,2,4]triazolo[1,5-a]pyridin-6-yl-1H-imidazole-2-methanamine); LY2109761 (7-(2-morpholinoethoxy)-4-(2-(pyridin-2-yl)-5,6-dihydro-4H-pyrrolo[1,2-b]pyrazol-3-yl)quinoline); SB505124 (2-(4-(benzo[d][1,3]dioxol-5-yl)-2-tert-butyl-1H-imidazol-5-yl)-6-methylpyridine); LY364947 (quinoline, 4-[3-(2-pyridinyl)-1H-pyrazol-4-yl]); SB431542 (4-(4-(benzo[d][1,3]dioxol-5-yl)-5-(pyridin-2-yl)-1H-imidazol-2-yl)benzamide); K02288(3)-[(6-Amino-5-(3),4,5-trimethoxyphenyl)-3-pyridinyl]phenol]; or LDN-212854 (quinoline, 5-[6-[4-(1-piperazinyl) phenyl]pyrazolo[1,5-a]pyrimidin-3-yl]), and preferably Repsox, but the ALK-5 kinase inhibitor is not limited thereto. The medium of the present disclosure may contain an ALK-5 kinase inhibitor in the range of 0.01 μM to 20 μM, preferably 0.1 μM to 10 μM, more preferably 0.5 μM to 5 μM, and most preferably 0.7 μM to 1.5 μM.

In the present disclosure, the term "hedgehog inhibitor" may preferably be a sonic hedgehog inhibitor, more preferably cyclopamine, mifepristone, GDC-0449 (vismodegib), XL139 (BMS-833923), IPI926, IPI609 (IPI269609), LDE225, jervine, GANT61, permorphamine, SAG, SANT-2, tomatidine, SANT74, SANT75, zerumbone or derivatives thereof, but the hedgehog inhibitor is not limited thereto. The medium of the present disclosure may contain a hedgehog inhibitor in the range of 0.05 μM to 20 μM, preferably 0.1 μM to 15 μM, more preferably 0.5 μM to 10 μM, even more preferably 0.5 μM to 5 μM, and most preferably, 1 μM to 3 μM.

In the present disclosure, the term "MAPK inhibitor" refers to mitogen activated protein kinases [a mitogen activated protein kinase; MAPK], which is a member of the prolinergic serine/threonine kinase family that activates their substrates by double phosphorylation. Known MAPK inhibitors, which are P38 kinase inhibitors, may be 1-pyridinyl-2-phenylazole, SB 203580, SKF 86002, SKF 86096, SKF 104351, 1-aryl-2-pyridinyl/pyrimidinyl heterocycles, SB 242235, RO-3001195, SX-011, or BIRB-796, but the MAPK inhibitor is not limited thereto, and is described in G. J. Hanson (*Expert Opinions on Therapeutic Patents,* 1997, 7, 729-733), J Hynes et al. (*Current Topics in Medicinal Chemistry,* 2005, 5, 967-985), C. Dominguez et al. (*Expert Opinions on Therapeutics Patents,* 2005, 15, 801-816), and L. H. Pettus & R. P. Wurtz (*Current Topics in Medicinal Chemistry,* 2008, 8, 1452-1467). The MAPK inhibitor of the present disclosure may preferably be sb203580, but is not limited thereto. The medium of the present disclosure may contain a MAPK inhibitor in the range of 50 μM to 5,000 s, 0.001 to 2,500 μM, 0.01 μM to 1,000 μM, 0.01 μM to 900 M, 0.01 μM to 800 μM, 0.01 μM to 700 μM, 0.01 μM to 600 μM, 0.01 μM to 500 μM, 0.01 μM to 400 μM, 0.01 μM to 300 μM, 0.01 μM to 200 μM, 0.01 μM to 100 μM, 0.01 μM to 90 μM, 0.01 μM to 80 μM, 0.01 μM to 70 μM, 0.01 μM to 60 μM, 0.01 μM to 50 μM, 0.01 μM to 40 μM, 0.01 μM to 30 μM, 0.01 μM to 20 μM, 0.01 μM to 10 μM, 0.01 μM to 5 μM, 0.01 μM to 3 μM, 0.01 μM to 2 μM, 0.01 μM to 1 μM, 0.5 μM to 10 μM, 0.5 μM to 7 μM, 0.5 μM to 5 M, 0.5 μM to 3 μM, 0.5 μM to 1.5 μM, 0.7 μM to 1.3 μM, or about 1 μM.

As used herein, the term "calcium channel agonist" is also referred to as "calcium channel opener" and is not limited as long as it is a material that promotes ion transfer through a calcium channel. The calcium channel agonist of the present disclosure may be one or more selected from the group consisting of Bay K-8644, FPL 64179, and CGP28392, but is not limited thereto. The medium of the present disclosure may contain the calcium channel agonist in the range of 0.05 μM to 20 μM, preferably 0.1 μM to 15 μM, more preferably 0.5 μM to 10 μM, even more preferably 0.5 μM to 5 μM, and most preferably 1 μM to 3 μM.

As used herein, the term "GLP receptor agonist" may specifically be a GLP-1 receptor agonist, and may encompass all peptides having GLP action activity, fragments thereof, precursors thereof, variants or derivatives thereof, and may include materials capable of activating GLP receptors without limitation. The GLP receptor agonist of the present disclosure may be one or more selected from the group consisting of exendin-4, dulaglutide, exenatide, semaglutide, liraglutide, lixisenatide, and albiglutide, but is not limited thereto. The medium of the present disclosure may contain the GLP receptor agonist in the range of 1 ng/mL to 500 ng/mL, 1 ng/mL to 400 ng/mL, 1 ng/mL to 300 ng/mL, 1 ng/mL to 200 ng/mL, 1 ng/mL to 100 ng/mL, 30 ng/mL to 500 ng/mL, 30 ng/mL to 400 ng/mL, 30 ng/mL to 300 ng/mL, 30 ng/mL to 200 ng/mL, 30 ng/mL to 100 ng/mL, 30 ng/mL to 90 ng/mL, 30 ng/mL to 80 ng/mL, 30 ng/mL to 70 ng/mL, 40 ng/mL to 60 ng/mL, or about 50 ng/mL.

As used herein, the term "supplement" may be one or more selected from the group consisting of 2-phospho-L-ascorbic acid, B27, laminin, nicotinamide, and N2.

In addition, the present disclosure provides a method for direct reprogramming from somatic cells to pancreatic beta cells, which includes culturing somatic cells in the presence of a composition containing a MAPK inhibitor, a calcium channel agonist, a GLP receptor agonist, and a supplement, and one or more miRNA selected from the group consisting of miR-127 and miR-709.

In the present disclosure, the method may include or consist of the stages of (1) inducing somatic cells into pancreatic endoderm cells; (2) inducing the pancreatic endoderm cells into pancreatic progenitor cells; and (3) inducing the pancreatic progenitor cells into pancreatic beta cells, but is not limited thereto.

In the present disclosure, the method may include or consist of (3) inducing pancreatic progenitor cells into pancreatic beta cells, but is not limited thereto.

In the present disclosure, while when the somatic cells of the method are fibroblasts, differentiation is required through three stages, when the somatic cells are pancreatic duct cells and exocrine cells having the properties of pancreatic progenitor cells, somatic cells can be directly reprogrammed into pancreatic beta cells in the presence of the composition of (3).

In the present disclosure, the direct reprogramming method may include the following stages, but is not limited thereto:

(1) inducing somatic cells into pancreatic endoderm cells in the presence of a composition containing a histone methyltransferase inhibitor, activin A, and a supplement, and one or more miRNA selected from the group consisting of miR-127 and miR-709;

(2) inducing the pancreatic endoderm cells into pancreatic progenitor cells in the presence of a composition containing a retinoic acid agonist, an ALK-5 kinase inhibitor, a hedgehog inhibitor and a supplement, and one or more miRNA selected from the group consisting of miR-127 and miR-709; and (3) culturing the somatic cells in the presence of a composition containing a MAPK inhibitor, a calcium channel agonist, a GLP receptor agonist, and a supplement, and one or more miRNA selected from the group consisting of miR-127 and miR-709.

Stage (1) of the present disclosure may be performed without limitation as long as it is a period capable of inducing differentiation into pancreatic beta cells, but may be performed for 3 to 10 days, 4 to 9 days, 4 to 8 days, 4 to 7 days, or 5 to 7 days, and more preferably, may be performed or about 6 days. The supplement in the above stage may preferably be 2-phospho-L-ascorbic acid.

The culture of Stage (2) may be performed without limitation, but may be performed for 0.5 to 8 days, 0.5 to 7 days, 1 to 7 days, 2 to 6 days, 3 to 5 days, or about 4 days. However, the cultivation period is not limited thereto. The supplement of Stage (2) may preferably be 2-phospho-L-ascorbic acid.

Stage (3) of the present disclosure may be performed without limitation as long as the period during which the differentiation-induced cells can mature, but may be performed for 7 to 13 days, 8 to 12 days, 9 to 11 days, or about 10 days. However, the cultivation period is not limited thereto. The supplement in the above stage may preferably be one or more selected from the group consisting of 2-phospho-L-ascorbic acid, laminin, B27, and nicotinamide, and more preferably 2-phospho-L-ascorbic acid, laminin, B27, and nicotinamide.

In the case of using the direct reprogramming method of the present disclosure, there is an advantage in that there is no possibility of cancer occurrence while not having increased immune rejections, compared to the conventionally known stem cell differentiation method and chemical cell differentiation method.

The term "medium" of the present disclosure may refer to a basic medium known in the art without limitation. The basal medium may be artificially synthesized and prepared, or a commercially prepared medium may be used. Examples of commercially prepared media include Dulbecco's Modified Eagle's Medium (DMEM), Minimal Essential Medium (MEM), Basal Medium Eagle (BME), RPMI 1640, F-10, F-12, α-Minimal essential Medium (α-MEM), Glasgow's Minimal Essential Medium (G-MEM), Iscove's Modified Dulbecco's Medium, etc., but is not limited thereto, and it may be a DMEM medium.

The culture solution for culturing the somatic cells includes all of the culture solution for medium commonly used for culturing fibroblasts in the art. The culture medium used for culture generally contains a carbon source, a nitrogen source, and a trace element component.

In addition, the present disclosure provides a kit for inducing direct reprogramming of somatic cells into pancreatic beta cells, which includes a composition containing one or more miRNA selected from the group consisting of miR-127 and miR-709.

In the present disclosure, the kit may further include a cell culture dish, but is not limited thereto.

The cell culture dish refers to a cell culture vessel and it includes a cell culture vessel regardless of the material, size, and shape of the culture dish. The cell culture dish may be a culture dish for suspension culture or a culture dish for adherent culture.

Most methods of inducing somatic cells into pancreatic beta cells using direct reprogramming(direct conversion) are performed by introducing a foreign gene. However, introduction of a gene using a virus causes genomic instability due to random integration of foreign genes; therefore, there is a possibility that it may cause occurrence of cancer when clinically applied to patients in the future. For this reason, methods using small molecules without injecting foreign genes have been gradually proposed. Nevertheless, at least one gene is being used, and without gene introduction, it is still not possible to convert a human somatic cell into a desired cell.

However, the present disclosure is a method for securing genetic stability for inducing pancreatic beta cells from a patient's somatic cells by treating with microRNA or a composition combining microRNA and a small molecule without introducing a foreign gene, and the method was designed to lower the possibility of cancer development, which is a problem in the existing cell conversion method using a gene, while fundamentally solving the genetic defect.

In the present disclosure, somatic cells were directly differentiated into pancreatic beta cells using micro RNA alone or a combination of a small molecule and microRNA. Accordingly, the microRNA of the present disclosure itself may be used as a therapeutic agent for diabetes or pancreatic cancer, and it can be prepared into a cellular therapeutic agent for patients thus having a very high application potential.

Accordingly, the present disclosure relates to a pharmaceutical composition for preventing or treating diabetes or pancreatic cancer, which contains one or more miRNA selected from the group consisting of miR-127 and miR-709 as an active ingredient.

In addition, the present disclosure provides a cellular therapeutic agent for the treatment of diabetes or pancreatic cancer, which contains as an active ingredient pancreatic beta cells induced to undergo direct reprogramming by the direct reprogramming method.

In addition, the present disclosure provides a method for preventing or treating diabetes or pancreatic cancer, which includes delivering a composition containing one or more miRNA selected from the group consisting of miR-127 and miR-709 into the living body to induce direct reprogramming of somatic cells into beta cells in vivo.

"Diabetes", which is the subject for treatment or prevention in the present disclosure, is a metabolic disorder syndrome characterized by a deficiency of insulin hormone produced in beta cells of the pancreas or abnormal insulin resistance, and hyperglycemia caused by both of these defects. Such diabetes can be divided into insulin-dependent diabetes mellitus (IDDM, type 1) and non-insulin-dependent diabetes mellitus (NIDDM, type 2) caused by insulin resistance and impaired insulin secretion. In both type 1 and type 2 diabetes, various complications such as heart disease, intestinal disease, eye disease, neurological disease, and stroke can occur. This is because as long-term elevation of blood glucose levels and insulin levels cause chronic neurological disease and cardiovascular disease, and acute complications are induced as a result of short-term hypoglycemia and hyperglycemia responses. Diabetes mellitus causes disorders in carbohydrate metabolism as well as lipid and protein metabolism as hyperglycemia continues chronically. The conditions, which are various and directly caused by hyperglycemia, include diabetic peripheral neuropathy, diabetic retinopathy, diabetic nephropathy, diabetic cataract, keratosis, diabetic arteriosclerosis, etc. in the retina, kidney, nerves, and cardiovascular system.

One of the important pathological phenomena that cause and deepen diabetes is the death of pancreatic β-cells due to hyperglycemia. The present inventors provide a method for producing beta cells usable for the treatment of diabetes by converting somatic cells into pancreatic beta cells. Accordingly, diabetes in the present disclosure may be a target if it is diabetes induced by glucose toxicity or deep or advanced diabetes, and more specifically, it may be selected from the group consisting of type 1 diabetes, type 2 diabetes, and gestational diabetes.

"Delivery" of the present disclosure may be through administration, but is not limited thereto.

The miRNA of the present disclosure may be included in the form of a pharmaceutically acceptable salt. As used herein, the term "pharmaceutically acceptable salt" includes salts derived from pharmaceutically acceptable inorganic acids, organic acids, or bases.

Examples of suitable acids include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, gluconic acid, naphthalene-2-sulfonic acid, benzenesulfonic acid, etc. Acid addition salts can be prepared by conventional methods, for example, by dissolving a compound in an aqueous solution with an excess of acid, and precipitating the salt using a water-miscible organic solvent such as methanol, ethanol, acetone, and acetonitrile. In addition, acid addition salts can also be prepared by heating an equimolar amount of a compound and an acid or alcohol in water and then evaporating the mixture to dryness, or by suction filtration of the precipitated salt.

Salts derived from suitable bases may include alkali metals (e.g., sodium, potassium, etc.), alkaline earth metals (e.g., magnesium, etc.), ammonium, etc., but are not limited thereto. The alkali metal or alkaline earth metal salt can be obtained, for example, by dissolving a compound in an excess alkali metal hydroxide or alkaline earth metal hydroxide solution, filtering the undissolved compound salt, and then evaporating and drying the filtrate. In particular, as the metal salt, it is pharmaceutically suitable to prepare a sodium, potassium, or calcium salt, and the corresponding silver salt can be obtained by reacting an alkali metal or alkaline earth metal salt with a suitable silver salt (e.g., silver nitrate).

The content of the miRNA in the composition of the present disclosure may be appropriately adjusted according to the symptoms of the disease, the degree of progression of the symptoms, the condition of the patient, etc., for example, 0.00001 wt % to 99.9 wt %, or 0.001 wt % to 50% wt % based on the total weight of the composition, but is not limited thereto. The content ratio is a value based on the dry amount from which the solvent is removed.

The pharmaceutical composition according to the present disclosure may further include suitable carriers, excipients, and diluents commonly used in the preparation of pharmaceutical compositions. The excipient may be, for example, one or more selected from the group consisting of a diluent, a binder, a disintegrant, a lubricant, an adsorbent, a humectant, a film-coating material, and a controlled-release additive.

The pharmaceutical composition according to the present disclosure may each be formulated, according to a conventional method, in powders, granules, sustained-release granules, enteric granules, liquids, eye drops, elixirs, emulsions, suspensions, alcohols, troches, fragrances, and limonade, tablets, sustained-release tablets, enteric tablets, sublingual tablets, hard capsules, soft capsules, sustained-release capsules, enteric capsules, pills, tinctures, soft extracts, dry extracts, fluid extracts, injections, capsules, perfusates, plasters, lotions, pastes, sprays, inhalants, patches, sterile injection solutions, and preparations for external use (e.g., aerosols), and used, and the preparations for external use may have formulations such as creams, gels, patches, sprays, ointments, plasters, lotions, liniments, pastes, and cataplasmas.

Carriers, excipients, and diluents that may be included in the pharmaceutical composition according to the present disclosure may include lactose, dextrose, sucrose, oligosaccharide, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

In the case of formulation, the pharmaceutical composition is prepared using commonly used diluents or excipients such as fillers, extenders, binders, humectants, disintegrants, surfactants, etc.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC), HPMC 1928, HPMC 2208, HPMC 2906, HPMC 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol (PEG) 4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives for the liquid formulation according to the present disclosure, water, diluted hydrochloric acid, diluted sulfuric acid, sodium citrate, monostearate sucrose, polyoxyethylene sorbitol fatty acid esters (Twinester), polyoxyethylene monoalkyl ethers, lanolin ethers, lanolin esters, acetic acid, hydrochloric acid, aqueous ammonia, ammonium carbonate, potassium hydroxide, sodium hydroxide, prolamine, polyvinylpyrrolidone, ethyl cellulose, sodium carboxymethyl cellulose, etc. may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

Purified water may be used in the emulsion according to the present disclosure, and if necessary, an emulsifier, a preservative, a stabilizer, a fragrance, etc. may be used.

The suspending agents according to the present disclosure may include acacia, tragacantha, methylcellulose, carboxymethylcellulose, sodium carboxymethylcellulose, microcrystalline cellulose, sodium alginate, hydroxypropylmethylcellulose (HPMC), HPMC 1828, HPMC 2906, HPMC 2910, etc., and if necessary, a surfactant, a preservative, a stabilizer, a colorant, and a fragrance may be used.

The injections according to the present disclosure may include distilled water for injection, a 0.9% sodium chloride injection solution, a ringer's injection solution, a dextrose injection solution, a (dextrose+sodium chloride) injection solution, PEG, a lactated ringer' injection solution, solvents (e.g., ethanol, propylene glycol, non-volatile oil-sesame oil, cottonseed oil, peanut oil, soybean oil, corn oil, ethyl oleate, isopropyl myristate, and benzene benzoate); solubilizing aids (e.g., sodium benzoate, sodium salicylate, sodium acetate, urea, urethane, monoethyl acetamide, butazolidine, propylene glycol, the Tween series, amide nicotinate, hexamine, and dimethyl acetamide; buffers (e.g., weak acids and salts thereof(acetic acid and sodium acetate), weak bases and salts thereof (ammonia and ammonium acetate), organic compounds, proteins, albumin, peptone, and gums); isotonic agents (e.g., sodium chloride); stabilizers (e.g., sodium bisulfite ($NaHSO_3$), carbon dioxide gas, sodium metabisulfite ($Na_2S_2O_5$), sodium sulfite ($Na_2SO_3$), nitrogen gas ($N_2$), ethylenediaminetetraacetic acid); sulfating agents (e.g., 0.1% sodium bisulfide, sodium formaldehyde sulfoxylate, thiourea, disodium ethylenediaminetetraacetate, and acetone sodium bisulfite); analgesic agents (e.g., benzyl alcohol, chlorobutanol, procaine hydrochloride, glucose, and calcium gluconate); and suspending agents (e.g., CMC sodium, sodium alginate, Tween 80, and aluminum monostearate).

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan(propylene glycol monostearate), glycerin, Adeps solidus, buytyrum Tego-G, cebes Pharma 16, hexalide base 95, cotomar, Hydrokote SP, S-70-XXA, S-70-XX75(S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, etc., and these solid preparations are prepared by mixing at least one excipient in the extract, for example, starch, calcium carbonate, sucrose or lactose, gelatin, etc. Additionally, lubricants (e.g., magnesium stearate and talc) are also used in addition to simple excipients.

Liquid preparations for oral administration include suspending agents, solutions for internal use, emulsions, syrups, etc., and various excipients (e.g., humectants, sweeteners, fragrances, preservatives, etc.) may be included in addition to water and liquid paraffin, which are commonly used simple diluents. Preparations for parenteral administration include sterile aqueous solutions, non-aqueous solutions, a suspension, an emulsion, a freeze-dried preparation, and a suppository. As non-aqueous solvents and suspending agents, propylene glycol, polyethylene glycol, vegetable oils (e.g., olive oil), injectable esters (e.g., ethyl oleate), etc. may be used.

The pharmaceutical composition according to the present disclosure is administered in a pharmaceutically effective amount. As used herein, the term "pharmaceutically effective amount" refers to an amount sufficient to treat a disease at a reasonable benefit/risk ratio applicable to medical treatment, and the effective dose level may be determined according to the type and severity of the patient's disease, drug activity, sensitivity to the drug, administration time, administration route and excretion rate, duration of treatment, factors including drugs to be administered concurrently, and other factors well known in the medical field.

The pharmaceutical composition according to the present disclosure may be administered as an individual therapeutic agent, may be administered in combination with other therapeutic agents, may be administered sequentially or simultaneously with conventional therapeutic agents, and may be administered once or multiple times. In consideration of all of the above factors, it is important to administer an amount capable of obtaining the maximum effect with a minimum amount without side effects, which can easily be determined by those skilled in the art to which the present disclosure pertains.

The pharmaceutical composition of the present disclosure may be administered to a subject by various routes. All modes of administration may be considered, for example, oral administration, subcutaneous injection, intraperitoneal administration, intravenous injection, intramuscular injection, paraspinal space (intrathecal) injection, sublingual administration, buccal administration, rectal insertion, vaginal insertion, ocular administration, otic administration, nasal administration, inhalation, spray through the mouth or nose, dermal administration, transdermal administration, etc.

The pharmaceutical composition of the present disclosure is determined according to the type of drug as an active ingredient along with several related factors (e.g., the disease to be treated, route of administration, patient's age, sex, weight, and severity of the disease).

As used herein, the term "individual" refers to a subject in need of treatment for a disease, and is not limited as long as it is a vertebrate, specifically, is applicable to humans, mice, rats, guinea pigs, rabbits, monkeys, pigs, horses, cows, sheep, antelopes, dogs, cats, fish and reptiles.

As used herein, the term "administration" refers to provision of a predetermined composition of the present disclosure to a subject by any suitable method.

As used herein, the term "prevention" refers to all actions that inhibit or delay the onset of a target disease; the term "treatment" refers to all actions that improve or beneficially change a target disease and metabolic abnormalities thereof by the administration of the pharmaceutical composition according to the present disclosure; and the term "improvement" refers to all actions that reduce target disease-related parameters, for example, the degree of symptoms by the administration of the pharmaceutical composition according to the present disclosure.

In addition, the present disclosure relates to a method for preparing a cellular therapeutic agent for diabetes or pancreatic cancer, which includes mixing the pancreatic beta cells, whose differentiation was induced by the above method, with one or more selected from the group consisting of pharmaceutically acceptable carriers and excipients.

As used herein, the term "cellular therapeutic agent", which is a pharmaceutical drug used for the purpose of treatment, diagnosis, and prevention (US FDA Regulations) using cells and tissues isolated from humans, cultured, and prepared through special manipulation, refers to a pharmaceutical drug in which such cells are used for the purposes of treatment, diagnosis, and prevention of diseases through a series of actions such as proliferation and selection of living autologous, allogeneic, or xenogeneic cells in vitro or changing the biological characteristics of cells in other ways so as to restore the functions of the cells or tissue.

The cell therapy composition of the present disclosure may be administered through any general route as long as it can reach the target tissue. The cell therapy composition may be administered through parenteral administration (e.g., intraperitoneal administration, intravenous administration, intramuscular administration, subcutaneous administration, and intradermal administration), but the administration route is not limited thereto.

The composition may be formulated in a suitable form together with a pharmaceutical carrier commonly used for cell therapy. The term "pharmaceutically acceptable" refers to a composition, which is physiologically acceptable and does not normally cause allergic reactions (e.g., gastrointestinal disorders, dizziness, etc.) or similar reactions when administered to humans. Pharmaceutically acceptable carriers include, for example, carriers for parenteral administration (e.g., water, suitable oils, saline, aqueous glucose, glycol, etc.) and may further include stabilizers and preservatives. Suitable stabilizers include antioxidants (e.g., sodium hydrogen sulfite, sodium sulfite, and ascorbic acid). Suitable preservatives include benzalkonium chloride, methyl- or propyl-paraben and chlorobutanol. As other pharmaceutically acceptable carriers, reference may be made to those described in the following literature (Remington's Pharmaceutical Sciences, 19th ed., Mack Publishing Company, Easton, PA, 1995).

The cellular therapeutic agent according to the present disclosure may be prepared in a unit dose form by formulating using a pharmaceutically acceptable carrier and/or excipient according to a method that can easily be carried out by those skilled in the art to which the present disclosure pertains or may be prepared by incorporation into a multidose container. Pharmaceutically acceptable carriers included in the cellular therapeutic agent of the present disclosure are those commonly used in formulation, and they include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc., but are limited thereto not. The cellular therapeutic agent of the present disclosure may further include a lubricant, a humectant, an emulsifier, a suspending agent, a preservative, etc., in addition to the above components.

In addition, the composition may be administered by any device which is capable of transporting a cellular therapeutic agent to a target cell.

The composition of a cellular therapeutic agent of the present disclosure may contain a therapeutically effective amount of the cellular therapeutic agent for the treatment of a disease. The "therapeutically effective amount" means the amount of an active ingredient or pharmaceutical composition that induces a biological or medical response in a tissue system, animal, or human as considered by researchers, veterinarians, physicians, or other clinical studies, and it includes the amount that induces alleviation of the symptoms of the disease or disorder to be treated.

It is apparent to those skilled in the art that the cellular therapeutic agent included in the composition of the present disclosure will vary depending on the desired effect. Therefore, the optimal content of the cellular therapeutic agent can easily be determined by those skilled in the art, and the type of disease, severity of disease, content of other components contained in the composition, type of formulation, and the patient's age, weight, general health conditions, sex and diet, administration time, administration route and secretion rate of the composition, treatment period, and drugs used at the same time may be adjusted according to various factors. It is important to include an amount that can obtain the maximum effect with a minimum amount without side effects in consideration of all of the above factors. For example, the daily dose of the stem cells of the present disclosure may be administered in an amount of $1.0\times10^4$ cells/kg body weight to $1.0\times10^{11}$ cells/kg body weight, preferably $1.0\times10^5$ cells/kg body weight to $1.0\times10^9$ cells/kg body weight once or several divided doses. However, it should be understood that the actual dose of the active ingredient should be determined in light of several related factors such as the disease to be treated, severity of disease, route of administration, the patient's weight, age, and sex; therefore, the dose described above is not intended to limit the scope of the present disclosure in any way.

In addition, in the treatment method of the present disclosure, the composition containing the cellular therapeutic agent of the present disclosure as an active ingredient may be administered in a conventional manner via rectal, intravenous (i.v.) therapy, intraarterial, intraperitoneal, intramuscular, intrasternal, transdermal, topical, intraocular, or intradermal route.

The present disclosure provides a treatment method which includes administering to a mammal a therapeutically effective amount of the composition of the cellular therapeutic agent of the present disclosure. The term mammal as used herein refers to a mammal that is the subject of treatment, observation, or experimentation, and preferably refers to a human.

MODES FOR CARRYING OUT THE INVENTION

Hereinafter, preferred Examples are presented to help the understanding of the present disclosure. However, the following Examples are provided only to facilitate easier understanding of the present disclosure, and the content of the present disclosure is not limited by the following Examples.

EXAMPLES

Example 1. Experimental Preparation and Experimental Method 1-1. Cell Culture Cells were cultured in Dulbecco's Minimal Essential Medium (DMEM, Welgene) supplemented with exosome-depleted 15% fetal bovine serum (FBS) (Gibco), 1% penicillin-streptomycin (Welgene), and 55 μM β-mercaptoethanol (β-ME) (Sigma) and incubated at 37° C. under 5% $CO_2$ conditions.

1-2. Isolation of Exocrine Cells from Mice

Exocrine tissue was isolated from two 8-week-old male mice, referring to the literature [G. C. Chau, D. U. Im, T. M. Kang, J. M. Bae, W. Kim, S. Pyo, E.-Y. Moon, S. H. J. J. C. B. Um, mTOR controls ChREBP transcriptional activity and pancreatic β cell survival under diabetic stress, 216(7) (2017) 2091-2105.]. First, filtered collagenase P (Roche) dissolved in HBSS (Hank's Balanced Salt Solution, Wellgene) at a concentration of 0.8 mg/mL was injected into the pancreas of the mice. The pancreatic tissue was incubated at 37° C. for 15 minutes with intermittent shaking. The digested suspension was filtered using a 400 μm mesh (Sigma), and all exocrine cells were isolated from islets using density gradient centrifugation on a Biocoll separation solution (Merck-Millipore). Then, the cells were centrifuged at 2,000 rpm at 20° C. for 20 minutes. The top layer of the Biocoll gradient contained acinar cells, whereas the pellet contained all other cells including pancreatic ductal cells excluding islets and acinar cells. Acinar cells and pancreatic ductal cells were carefully collected, mixed together, and filtered through a 70 μm mesh (Falcon). Then, the cells were washed 3 times with 1×HBSS and centrifuged at 1,200 rpm at 4° C. for 3 minutes, inoculated into 10 cm tissue culture dishes (TPP) containing Roswell Park Memorial Institute (RPMI) medium supplemented with 10% FBS and 1% penicillin/streptomycin (P/S), and incubated under 95% air and 5% $CO_2$.

1-3. Transfection

MEFs ($5\times10^4$ cells/well per 12-well plate) were transfected using the jetMESSENGER (Polyplus-Transfection, Illkirch, France) reagent according to the manufacturer's instructions. The miRNA to be infected (200 nM) (QIAGEN, Hilden, Germany) was diluted in mRNA buffer and 2 μL of the jetMESSENGER reagent was added thereto. The mixture was incubated at room temperature for 20 minutes and then added to MEFs, and 24 hours thereafter, a stage-specific medium was added thereto.

266-6 cells ($8\times10^4$ cells/well) were transfected using the RNAiMAX reagent (Thermo Fisher Scientific, Inc., Waltham, MA, USA) according to the manufacturer's protocol. Transfections were performed in a stage-specific medium and transfected cells were incubated for the desired length of time.

1-4. Immunostaining

After completion of the three-stage differentiation, differentiated β-like cells were obtained and immunostained as previously described (*Int. J. Mol. Sci.* 2020, 21, 665). Samples were visualized using a fluorescence microscope (IX71S1F3, Olympus, Tokyo, Japan). Antibodies used are shown in Table 1 below.

TABLE 1

| Antibody | Dilution used | Company | Catalog number | Purpose |
|---|---|---|---|---|
| Pdx1 | 1:100 | R&D systems | AF2419 | IF |
| Ngn3 | 1:100 | Millipore | AB5684 | IF |
| C-peptide | 1:200 | Cell Signaling Technology | 4593S | IF |
| β-actin | 1:1000 | Cell Signaling Technology | 4967S | WB |
| CD9 | 1:1000 | Abcam | ab92726 | WB |
| TSG101 | 1:1000 | Abcam | ab83 | WB |
| Alix | 1:1000 | Abcam | ab117600 | WB |
| Calnexin | 1:1000 | Abcam | ab22595 | WB |

1-5. MEF Direct Reprogramming to Pancreatic Lineage Using microRNA

As shown in FIG. 1, direct reprogramming of mouse embryonic fibroblasts (MEFs) was performed by modifying the existing protocol. For direct reprogramming of cells, knockout DMEM (KO-DMEM) (Gibco) was used as a basal medium. The knockout DMEM includes 15% knockout serum replacement (Gibco, Thermo Fisher Scientific, Inc., Waltham, MA, USA), 5% FBS (exosome depleted), 1% GlutaMax (Gibco, Thermo Fisher Scientific, Inc., Waltham, MA, USA), 1% Non-Essential Amino Acids (NEAA, Gibco, Thermo Fisher Scientific, Inc., Waltham, MA, USA), and 0.5 mM β-ME (Sigma Aldrich, Inc., Saint Louis, MO, USA).

The three-stage differentiation protocol of the present disclosure is as follows: Stage 1, differentiation from MEFs into pancreatic endoderm cells; Stage 2, differentiation of pancreatic endoderm cells into pancreatic progenitor-like cells; Stage 3, differentiation from pancreatic progenitor-like cells into beta-cell-like cells.

First, $5\times10^4$ MEF cells/well were seeded in a 12-well tissue culture plate of DMEM containing 10% FBS and 1×P/S for one day. The next day, a Stage 1 differentiation medium was added thereto. The Stage 1 differentiation medium contains 1 μM Bix-01294 (MedchemExpress, Monmouth Junction, NJ, USA), 280 μM 2-phospho-L-ascorbic acid (pVC) Sigma Aldrich, Inc., Saint Louis, MO, USA), and 50 ng/mL activin A (R&D Systems, Minneapolis, MI, USA). After addition of the medium, cells were maintained for 6 days. The medium used was replaced every 3 days. After 6 days, a Stage 2 differentiation medium was added for 4 days. The Stage 2 differentiation medium contains, as a small molecule, 0.5 nM TTNPB (MedchemExpress, Monmouth Junction, NJ, USA), 1 μM repsox (MedchemExpress, Monmouth Junction, NJ, USA), 2 μM cyclopamine (Tocris, Bristol, UK), and 280 μM pVc.

A Stage 3 differentiation medium contains 1 μM SB203580 (MedchemExpress, Monmouth Junction, NJ, USA), 1× Insulin-Transferrin-Selenium (ITS, Gibco, Thermo Fisher Scientific, Inc., Waltham, MA, USA), 10 mM nicotinamide (Sigma Aldrich, Inc., Saint Louis, MO, USA), 1 μg/mL laminin (Sigma Aldrich, Inc., Saint Louis, MO, USA), 50 ng/mL exendin-4 (MedchemExpress, Monmouth Junction, NJ, USA), 2 μM Bay K-8644 (Tocris, Bristol, UK), 1×B27 plus supplement (Gibco, Thermo Fisher Scientific, Inc., Waltham, MA, USA), and pVC. Cells were maintained for 10 days in the Stage 3 medium.

TABLE 2

| Stage | Stage Features | Medium Ingredients |
|---|---|---|
| Stage 1 | differentiation into endoderm cells | BIX01294 (BIX), phospho-L-ascorbic acid (pVC), activin A, and micro RNA |
| Stage 2 | differentiation into pancreatic progenitor cells | TTNPB, repsox, cyclopamine, pVC, and micro RNA |
| Stage 3 | differentiate into beta cells | SB203580, nicotinamide, Extendin-A, Bay K-8644, micro RNA |

TABLE 3

| Name | Sequence | SEQ ID NO |
|---|---|---|
| miR-127-5p | CUGAAGCUCAGAGGGCUCUGAU | 1 |
| miR-709 | GGAGGCAGAGGCAGGAGGA | 2 |
| miR-127 MI0000154 precursor | CCAGCCUGCUGAAGCUCAGAGGGCUCUGAUUC AGAAAGAUCAUCGGAUCCGUCUGAGCUUGGCU GGUCGG | 3 |
| miR-709 MI0004693 precursor | UGUCCCGUUUCUCUGCUUCUACUCAGAAGUGC UCUGAGCAUAGAACUGUCCUGUUUGAGCAGCA CUGGGGAGGCAGAGGCAGGAGGAU | 4 |
| miR-19b | ugugcaaauccaugcaaaacuga | 5 |

1-6. Studies of Gene Expression Using qRT-PCR

Total cellular RNA was extracted using the manufacturer's Trizol (Invitrogen) method. 1 μg of total RNA was used for cDNA synthesis using the PrimeScript 1st strand cDNA Synthesis Kit (Takara Clontech). The analysis of pancreatic lineage-specific markers was performed by the iQ SYBR Green Supermix (Biorad) using real time PCR (Biorad). The qRT-PCR conditions were 40 cycles of 30 seconds at 95° C., 15 seconds at 60° C., and 15 seconds at 72° C. The primers used in this study are shown in Table 4 below.

TABLE 4

| Gene Name | Forward Primer (5'-3') | Reverse Primer (5'-3') |
|---|---|---|
| Ngn3 | CAGTCACCCACTTCTGCTTC | GAGTCGGGAGAACTAGGATG |
| Nkx6 I | CTTCTGGCCCGGAGTGATG | GGGTCTGGTGTGTTTTCTCTTC |
| Pdx1 | CTTAACCTAGGCGTCCCACAA | GAAGCTCAGGGCTGTTTTTCC |
| Insulin-1 | GACCAGCTATAATCAGAGACCATC | GTAGGAAGTGCACCAACACGG |
| Insulin-2 | GGCTTCTTCTACACACCCAT | CCAAGGTCTGAAGGTCACCT |
| Glucagon | AGGGACCTTTACCAGTGATGT | AATGGCGACTTCTTCTGGGAA |
| Elastase1 | CGTGGTTGCAGGCTATGACAT | TTGTTAGCCAGGATGGTT |
| Cytokeratin 19 | CCTCCCGAGATTACAACCACT | GGCGAGCATTGTCAATCTGT |
| β-actin | GGCACCACACCTTCTACAATG | CCATGCCTGTGATTTGCAGTA |

1-7. Statistical Analysis

Statistical significance was determined by a two-way, paired student's t-test. The data indicated were obtained through three independent experiments and are presented as mean±SEM. $p<0.05$ was considered statistically significant. Statistical analysis was performed using Prism v8.0 (GraphPad Software, Inc., San Diego, CA, USA).

Example 2. Conversion of MEFs into β-Like Cells Using microRNA

The study of converting dox-induced MEFs into cell-like endoderm using small molecule compounds and generating functional pancreatic beta-cell-like cells provided the basis for a direct reprogramming approach. Accordingly, the present inventors presumed that if microRNA acts as a material for changing transcription, it will induce changes in pancreatic (endocrine)-specific transcription in MEF in Stage 1 medium depending on the presence/absence of small molecules (e.g., an epigenetic modifier BIX01294 and pVC).

As shown in FIG. 1*a*, the differentiation protocol for small molecule compounds includes three stages: Stage 1, conversion of MEFs into pancreatic endoderm cells (PECs); Stage 2, conversion of PEC into pancreatic progenitor-like cells (PPLC); and Stage 3, conversion of PPLCs into β-like cells (BLCs).

Figure 1B:
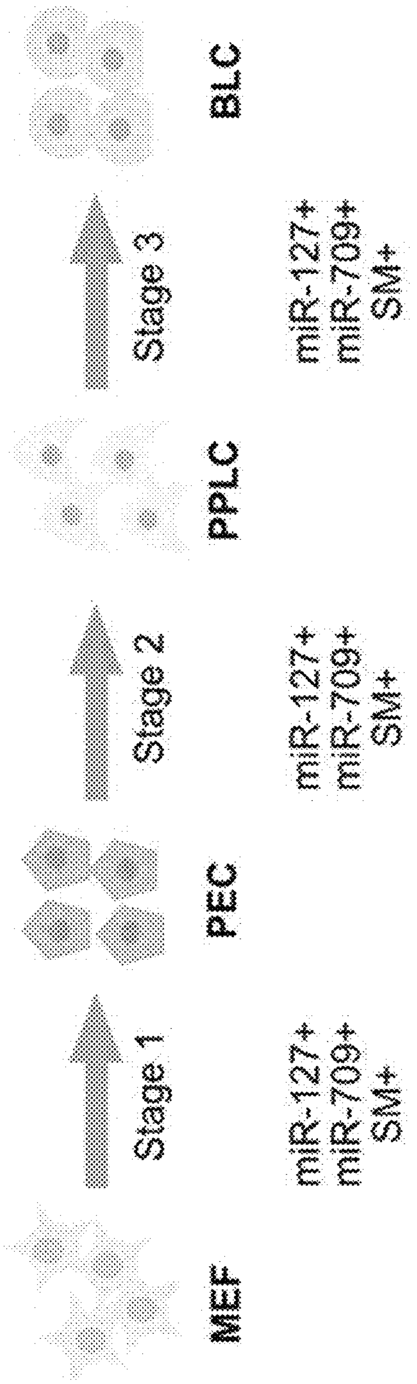
FIG. 1*b* shows a diagram illustrating a method in which microRNA is additionally added to the conversion condition using a small molecule.

The present inventors have established a final protocol of adding microRNAs to the three-stage protocol of FIG. 1*a* (see FIG. 1*b*).

Meanwhile, the increased expression of PDX1 indicates that the pancreas-specific program began compared to microRNA-untreated cells. The formation of the pancreas begins with the differentiation of definitive endoderm into pancreatic endoderm. Pancreatic endoderm cells express PDX1, which is a pancreatic-duodenal homeobox gene. In the absence of PDX1, the pancreas cannot develop beyond the formation of ventral and dorsal buds. Therefore, PDX1 expression characterizes an important stage in pancreatic organogenesis. Mature pancreas includes exocrine and endocrine tissues, among other cell types. Exocrine and endocrine tissues are generated from the differentiation of pancreatic endoderm. Accordingly, the present inventors have confirmed the expression of Pdx1 in order to confirm the differentiation into pancreatic beta-cell-like cells.

Figure 1C:
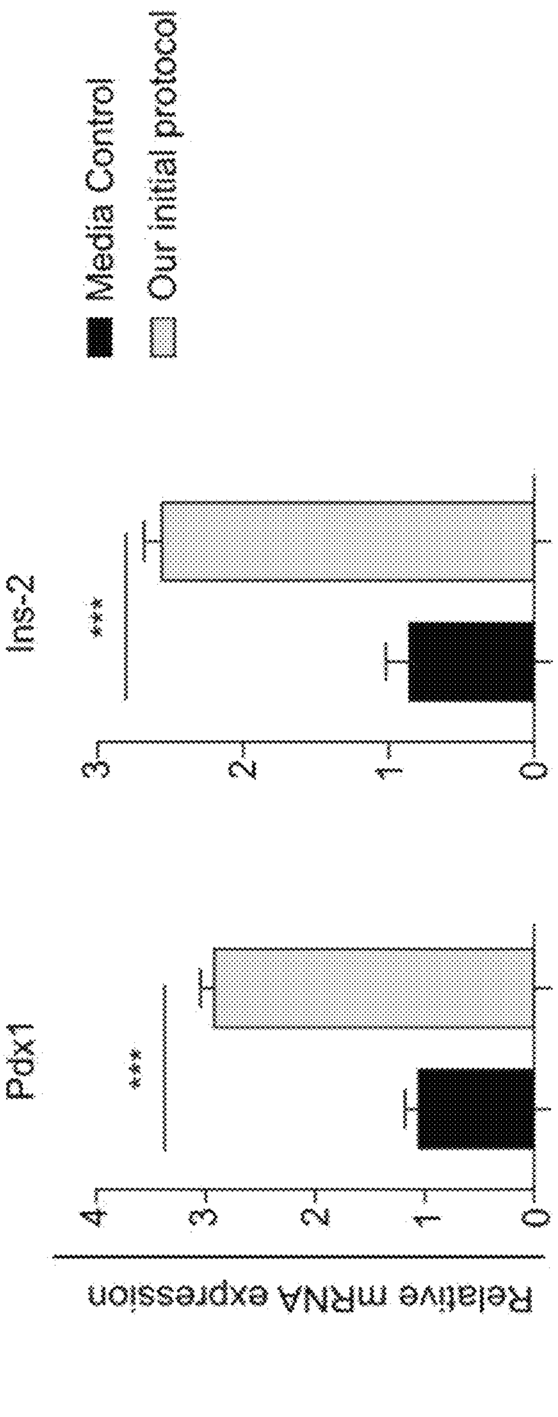
FIG. 1*c* shows graphs illustrating the overexpression of beta cell markers Pdx1 and Ins-2 in beta cells which were converted using a small molecule.

As shown in FIG. 1*c*, when the differentiation protocol for small molecule compounds of FIG. 1*a* was used compared to using the control medium (use of a basal medium), it was confirmed in MEFs that the expression of Pdx1 and insulin-2 was induced by 2.9-fold and 2.6-fold.

Therefore, it was confirmed that the differentiation protocol for small molecule compounds of the present disclosure is suitable for direct reprogramming of pancreatic beta cells.

Example 3. Confirmation of Efficacy of Micro RNA Alone on Differentiation of pdx1

In previous studies, the present inventors have confirmed that MIN6-derived exosomes are not only rich in various miRNAs (e.g., miR-486, miR-127, miR-19b, miR-494, and miR-709), but also are related to the pancreatic lineage. Accordingly, the present inventors investigated whether these miRNAs can enhance the expression of pancreatic beta cell markers individually or in combination.

First, before transfecting MEFs with a miRNA mimic to simulate naturally occurring miRNAs, transfection experiments were optimized using a 5' fluorescein amidite (FAM) labeled control miRNA mimic. The control miRNA mimic used was that which had no homology with mice, rats, or human miRNA. In addition, in order to select miRNAs that induce higher levels of Pdx1 during Stage 1 differentiation, transfection was performed individually.

Figure 2A:
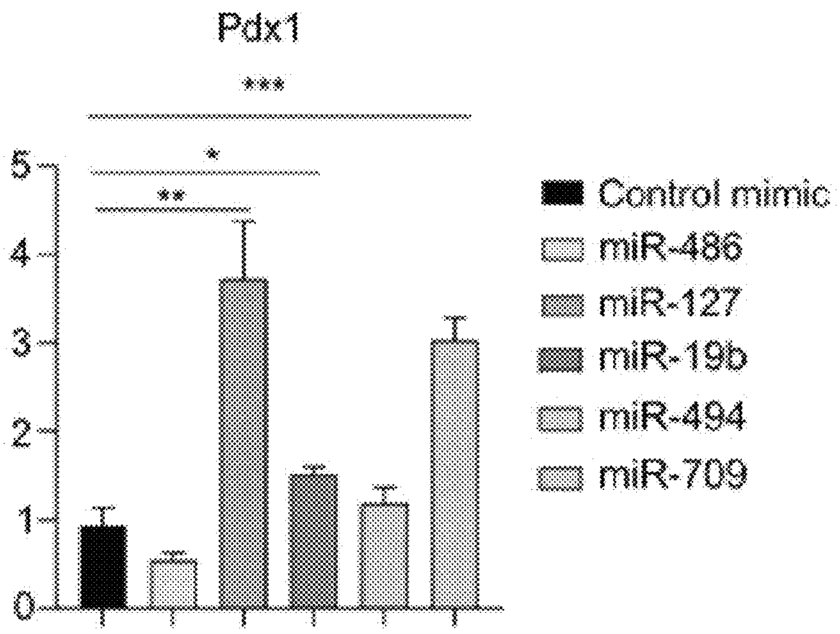
FIGS. 2*a* to 2*e* show the expression of major beta cell markers in the stage of differentiation from fibroblasts into β-cell-like cells. $*P<0.05$, $P<0.01$, and $*P<0.001$. Statistical significance was determined by a two-way, paired Student's t-test. Data shown represent mean f SEM from three independent experiments.

As shown in FIG. 2*a*, it was confirmed that miR-127 and miR-709 had the best effect of inducing expression of Pdx1 among various miRNAs. Specifically, it was shown that miR-127 induced 3.9-fold of the mimic, miR-709 induced 3.2-fold, and miR-19b induced 1.6-fold.

In the following examples, experiments were conducted using the three miRNAs having a large effect on inducing Pdx1 expression.

Example 4. Confirmation of Efficacy of microRNA Combination on Pdx1 Differentiation In Example 3, miR-127 and miR-709, which had a large effect on inducing Pdx1 expression, were combined at various concentrations and examined whether the combined miRNAs increase the expression of the pancreatic gene markers.

TABLE 5

| | miR-127 | miR-709 |
|---|---|---|
| Combination-1 | 100 nM | 100 nM |
| Combination-2 | 133 nM | 66 nM |
| Combination-3 | 66 nM | 133 nM |

Figure 2B:
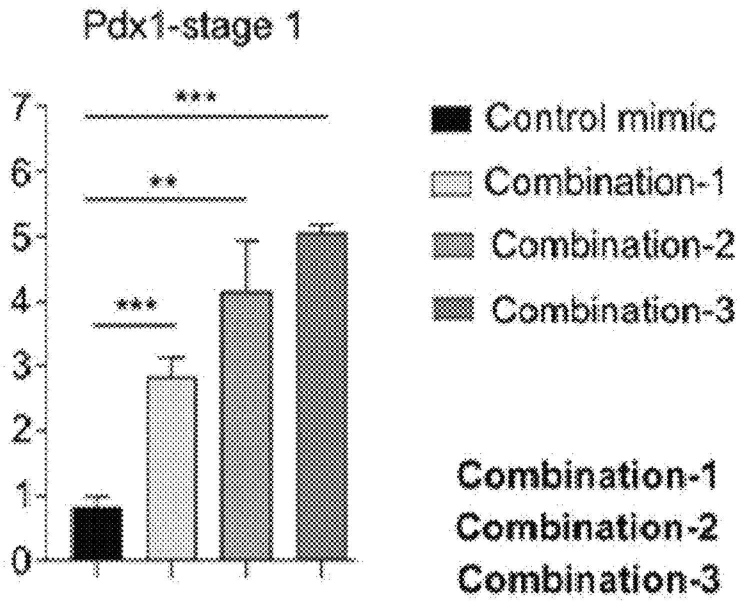

As shown in FIG. 2*b*, the highest transcription level of Pdx1 was observed in Stage 1 after the transfection with Combination-3 (miR-127+miR-709).

Figure 2C:
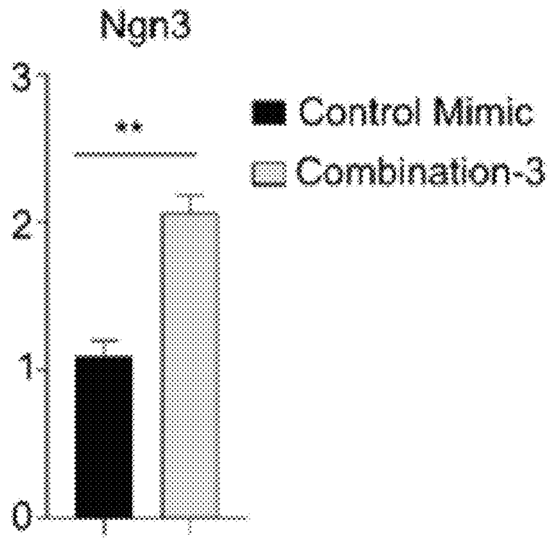

Additionally, as shown in FIG. 2*c*, it was confirmed that the expression level of Ngn3 was also significantly upregulated. It is known that early activation of Ngn3 exclusively induces glucagon-positive cells while depleting the pool of pancreatic progenitor cells.

Figure 2D:
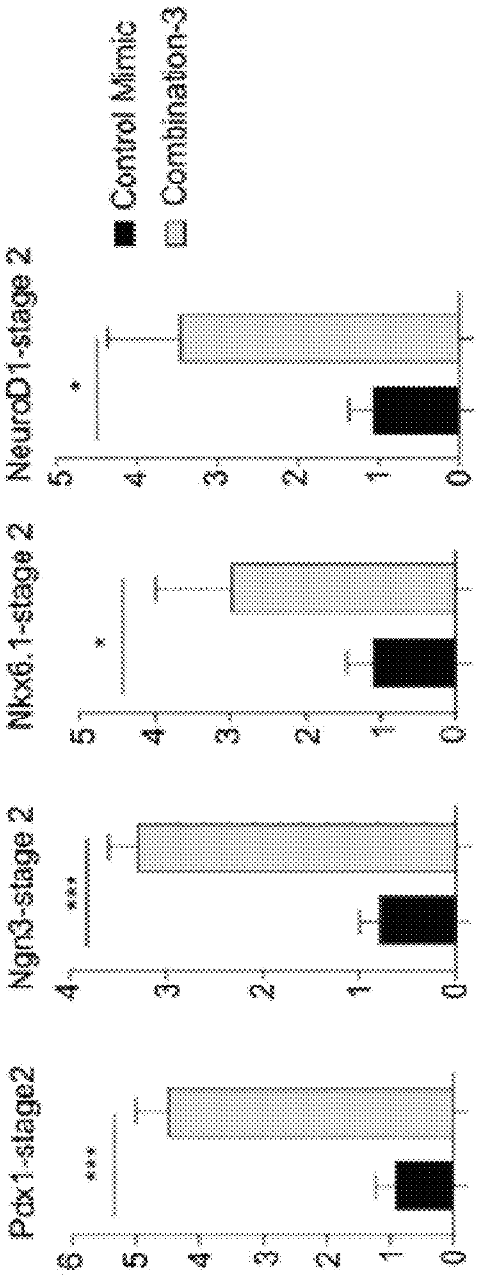

Additionally, as shown in FIG. 2*d*, after the transfection with Combination-3 (miR-127+miR-709), high levels of Pdx1, Ngn3, Nkx6.1, and NeuroD1 were observed even in Stage 2. In particular, Pdx1 and Ngn3 were increased 4.8-fold and 4.1-fold, respectively, compared to the mimic-treated group.

Figure 2E:
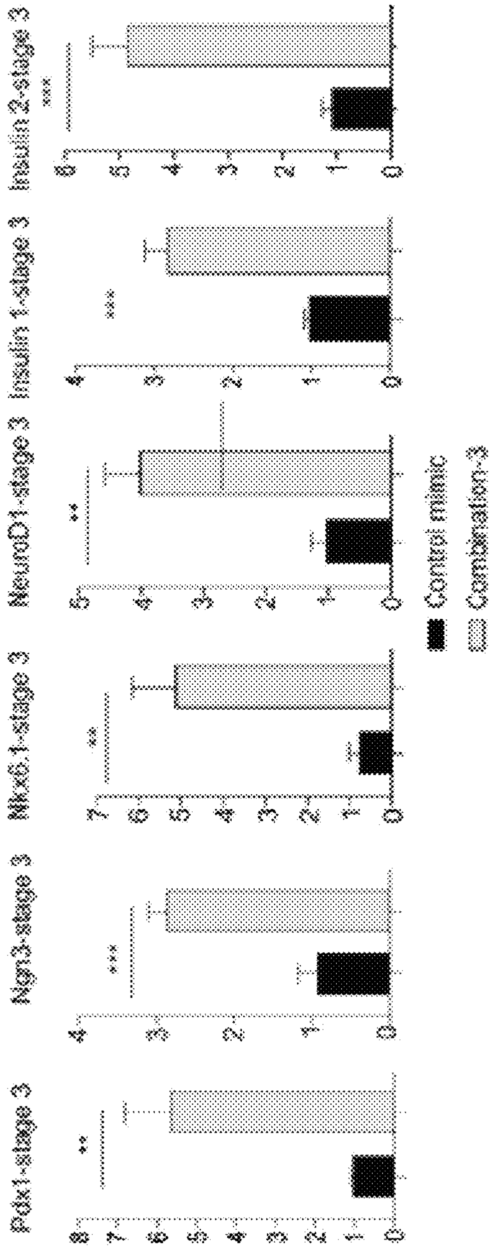

Additionally, as shown in FIG. 2*e*, it was confirmed that after the transfection with Combination-3 (miR-127+miR-709), the expression levels of pancreas-specific gene markers Pdx1 (5.4-fold), Ngn3 (2.8-fold), Nkx6.1 (including 6.2-fold), insulin-1 (2.7-fold), and insulin-2 (4.3-fold) were all significantly upregulated in Stage 3 cells compared to the mimic-treated group.

That is, these results indicate that as the stepwise treatment with miR-127 and miR-709 induces the differentiation of MEFs in the presence of small molecule compounds and improves the differentiation efficiency, MEFs can be differentiated into beta-like cells.

In addition, it was examined whether the expression of pancreatic gene markers was increased when miR-19b was co-treated in addition to miR-127 and miR-709.

TABLE 6

| | miR-127 | miR-709 | miR-19b |
|---|---|---|---|
| Combination-1 | 66 nM | 66 nM | 66 nM |
| Combination-2 | 160 nM | 20 nM | 20 nM |
| Combination-3 | 20 nM | 160 nM | 20 nM |
| Combination-4 | 20 nM | 20 nM | 160 nM |

Figure 3A:
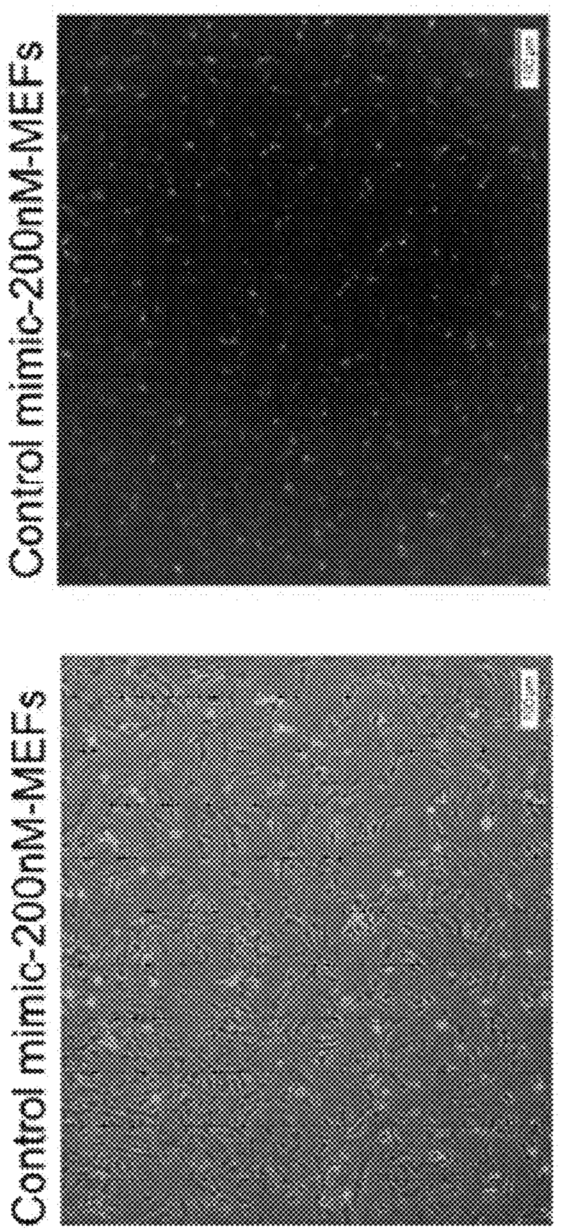
FIGS. 3*a* to 3*c* confirm the proliferative ability of mouse embryonic fibroblasts (MEF) following transfection with a miRNA mimic and combinations of miRNAs (miR-127, miR-709, and miR-19b) of the present disclosure.

First, as shown in FIG. 3*a*, as a result of performing a dose-dependent transfection, it was confirmed that miRNA provided about 80% transfection efficiency with low cytotoxicity when treated with a dose of 200 nM.

Figure 3B:
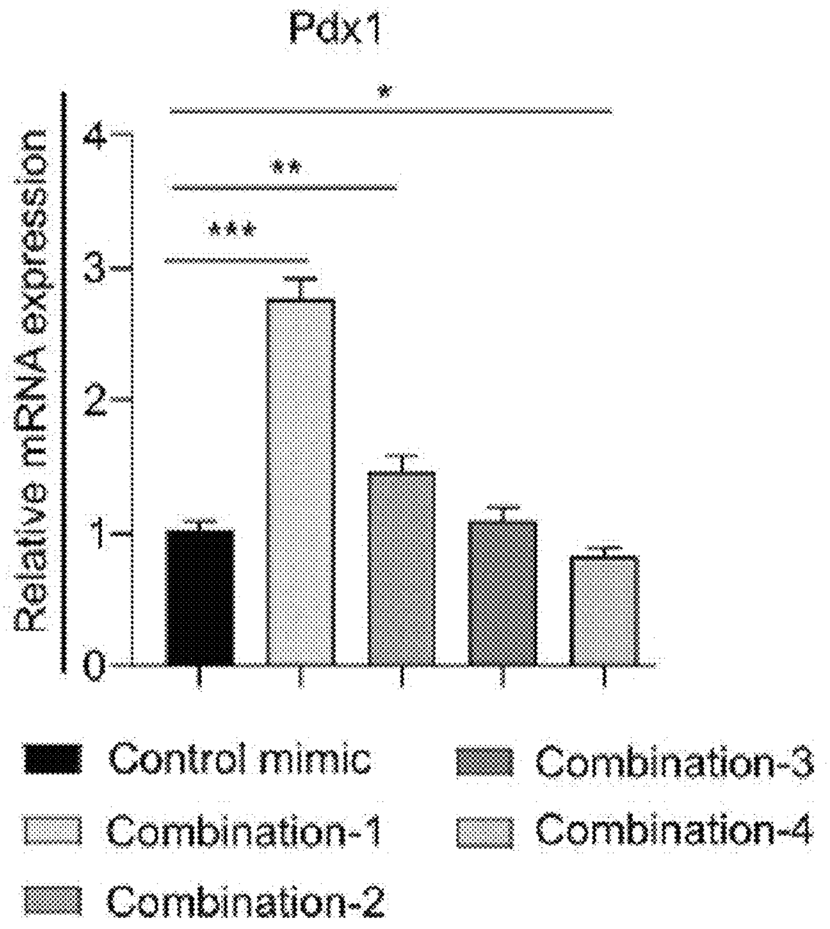

Additionally, as shown in FIG. 3*b*, the highest transcription level of Pdx1 was observed in Stage 1 after the transfection with Combination-1 (miR-127+miR-709+miR-19b).

Figure 3C:
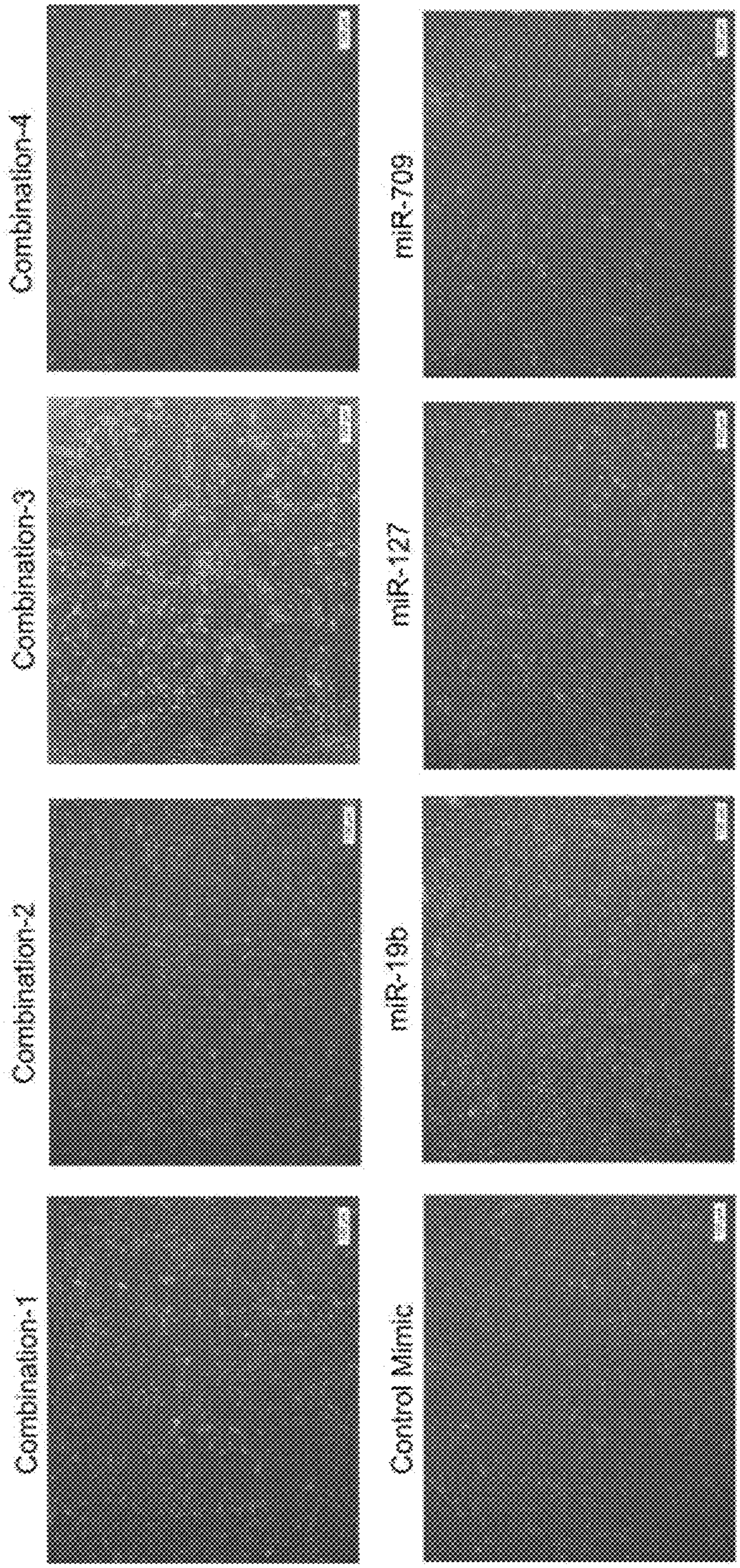

Additionally, as shown in FIG. 3*c*, it was confirmed that each different combination of miR-127+miR-709+miR-19b increases cell proliferation, and in particular, the highest cell proliferation was observed when transfected with only miR-19b and when transfected with Combination-3.

Example 5. Confirmation of Effect of Micro RNA Combination on Differentiation of Pancreatic Beta-Cell-Like Cells of Exocrine Cells The present inventors have confirmed that fibroblasts can be differentiated into pancreatic beta-cell-like cells using a combination of microRNAs of the present disclosure through Examples 3 and 4 above.

In addition thereto, since exocrine and endocrine cells of the pancreas share a common developmental pathway, the present inventors examined whether it is possible to differentiate into pancreatic beta-cell-like cells using exocrine cells.

First, mouse acinar cell line 266-6 cells were tested using Combination-3 (miR-127+miR-709). First, the isolated exocrine cells were aliquoted into a 6-well plate (coated with 1:10 dilution of Matrigel from BD Bioscience) in a Stage 3 medium. After placing one day in the Stage 3 medium, 50 μg/mL of microRNA was added to one well and not to the other well. After incubating the cells with microRNA in the Stage 3 medium for two days, fresh medium without microRNA was added to each well. After 7 days, cells for RNA isolation were collected using the Qiagen RNeasy kit, and gene profiling was performed using qRT-PCR.

Figure 4A:
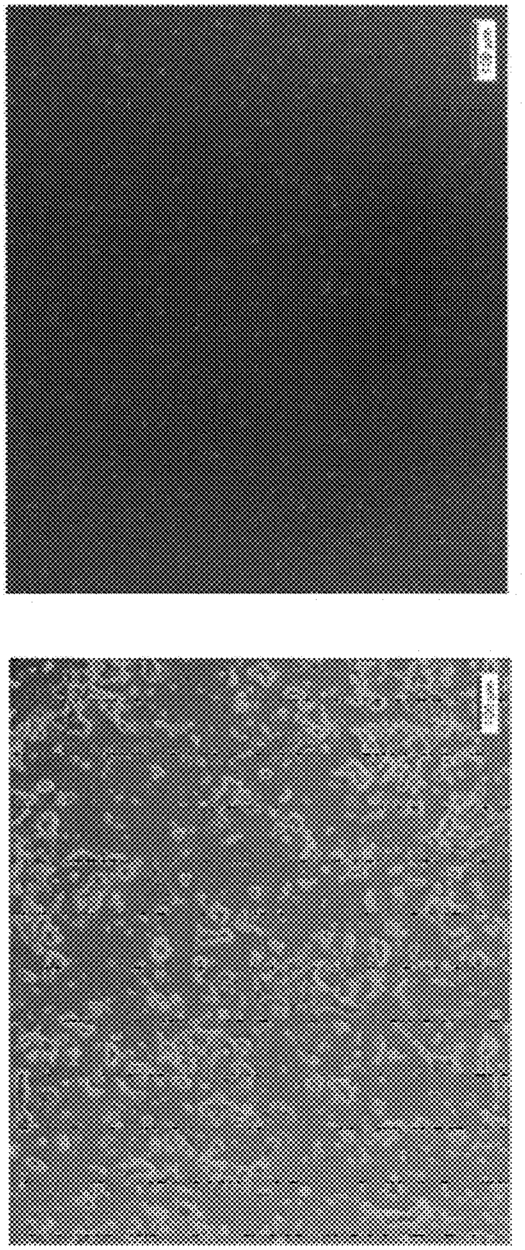
FIGS. 4*a* and 4*b* confirm the expression of pancreatic beta cell-related markers in an acinar cell 266-6, which is a type of exocrine cell, following transfection with a miRNA mimic and a combination of miRNAs (miR-127 and miR-709) of the present disclosure.

As shown in FIG. 4*a,* 266-6 cells showed transfection efficiency of 70-80% with the 5' FAM-labeled mimic control group.

Additionally, as the transfected 266-6 cells were cultured and grown in the Stage 3 medium, expression of the pancreatic beta cell markers was confirmed.

Figure 4B:
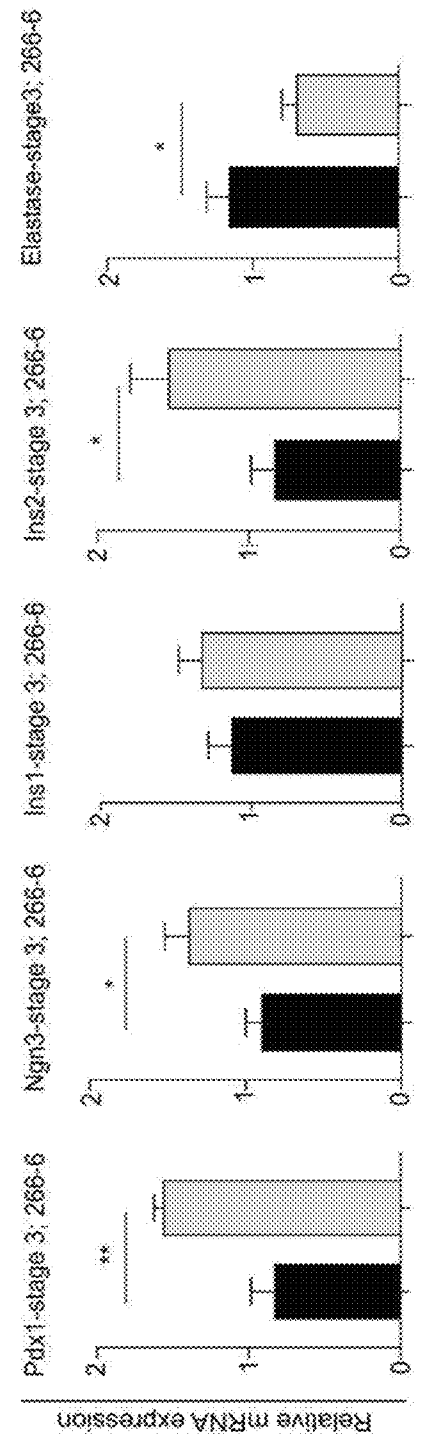

As shown in FIG. 4*b*, it was confirmed that the beta cell marker gene was increased even when exocrine cells were treated with a combination of microRNAs of the present disclosure. The level of Pdx1 was increased by 1.5-fold or more compared to untreated cells. Ngn3 expression was also upregulated by 1.6-fold in microRNA-treated cells. The levels of insulin-1 and insulin-2 were also increased by 1.8-fold and 1.9-fold, respectively. However, the expression of elastase (an acinar cell marker) was shown to be rather decreased when treated with microRNAs.

That is, it is possible to perform direct reprogramming of somatic cells (e.g., fibroblasts and exocrine cells) into pancreatic beta cells by a co-treatment of miR-127 and miR-709.

Example 6. Confirmation of Effect of Combination of Micro RNA and Small Molecule on Differentiation of Human Pancreatic Duct Cells into Beta-Cell-Like Cells The present inventors have confirmed that Capan-1, which are human pancreatic duct cells, can be differentiated into pancreatic beta-cell-like cells by a combination of miR-127 and a small molecule, and in addition thereto, the expression of pancreatic beta cell markers according to the presence or absence of the small molecule used in Stage 3 was confirmed.

Figure 5:
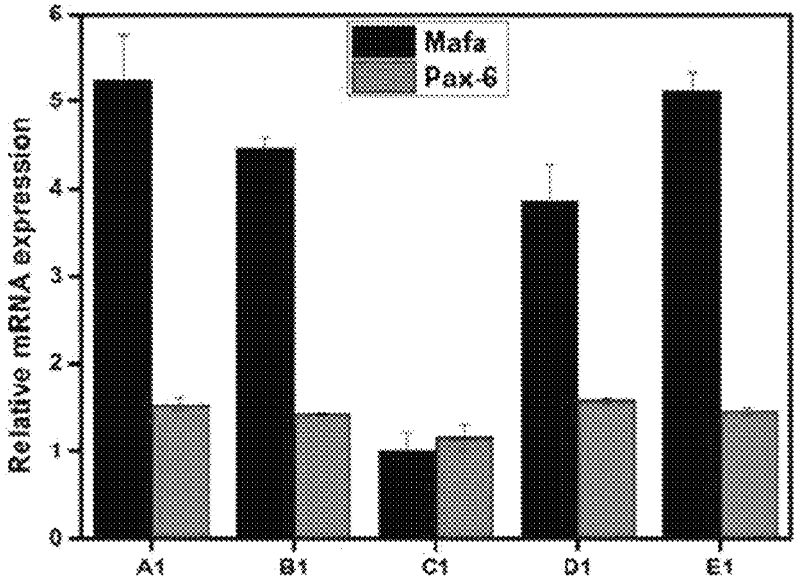
FIG. 5 shows the expression of a pancreatic beta-cell gene in Capan-1 cells (i.e., human pancreatic duct cells) according to the combination of miR-127 and a stage-3 small molecule. These are the measurement results of expression levels of Pax-6 and MafA (i.e., beta cell markers) obtained by using SB203580 (a MAP kinase inhibitor), nicotinamide (an adjuvant), exendin-4 (a GLP receptor agonist), and Bay K-8644 (a calcium channel agonist), which are small molecules used in stage-3, after treating with miR-127 in different combinations.

As shown in FIG. 5, it was confirmed that the expression of Pax-6 and MafA was significantly reduced by a Combination-C treatment which lacks nicotinamide.

This is a result indicating that nicotinamide is essential for the composition of the Stage 3 medium of the present disclosure.

Taken together, the present inventors have clearly found that when microRNA was used alone or microRNA and a small molecule are used in combination, direct reprogramming into pancreatic beta cells can be achieved. Therefore, the present disclosure provides a composition for inducing direct reprogramming of somatic cells into pancreatic beta cells, containing the microRNA of the present disclosure as an active ingredient; and it is expected that the thus generated pancreatic beta cells can be effectively used for the prevention, treatment, and improvement of pancreatic-related diseases such as diabetes or pancreatic cancer. Additionally, it is expected that this composition will be effectively used for the prevention, treatment, and improvement of pancreatic-related diseases (e.g., diabetes, pancreatic cancer, etc.) through the induction of beta cells of somatic cells in the body by directly injecting the composition for direct reprogramming into the body.

The description of the present disclosure described above is for illustration purposes, and those of ordinary skill in the art to which the present disclosure pertains would understand that it can easily be modified into other specific forms without changing the technical spirit or essential features of the present disclosure. Therefore, it should be understood that the embodiments described above are illustrative in all respects and not restrictive.

INDUSTRIAL APPLICABILITY

The present inventors attempted direct reprogramming by co-treatment of various small molecules (e.g., differentiation-inducing materials) and microRNAs, and as a result, they have found that the expression level of PDX1 in pancreatic beta cells was significantly increased, and that direct reprogramming was achieved in an extremely high yield when pancreatic beta cells were induced by such method. Additionally, the present disclosure has an advantage in that it has a low likelihood of cancer occurrence without generation of any immune rejection when transplanting converted pancreatic beta cells into patients with diabetes or pancreatic cancer due to the use of autologous cells; therefore, it is expected to be effectively used for the development of a safer cellular therapeutic agent and thus has industrial applicability.

The invention claimed is:

1. A method for direct reprogramming of somatic cells into pancreatic beta cells in vitro, which comprises culturing somatic cells in the presence of a composition comprising one or more microRNA selected from the group consisting of miR-127 and miR-709.

2. The method of claim 1, wherein the somatic cell is one or more selected from the group consisting of a fibroblast, a pancreatic ductal cell, and an exocrine cell.

3. The method of claim 1, wherein the composition further comprises miR-19b.

4. The method of claim 1, wherein the composition further comprises one or more small molecule selected from the group consisting of a histone methyltransferase inhibitor, a retinoic acid agonist; an ALK-5 kinase inhibitor; a hedgehog inhibitor; a MAPK inhibitor; a calcium channel agonist; a GLP receptor agonist; and a supplement.

5. The method of claim 4, wherein the histone methyltransferase inhibitor is one or more selected from the group consisting of BIX01294 (2-(Hexahydro-4-methyl-1H-1,4-diazepin-1-yl)-6,7-dimethoxy-N-[1-(phenylmethyl)-4-piperidinyl]-4-quinazolinamine), decitabine (5-aza-2'-deoxycytidine; DAC), zebularine, 3'-deazaneplanocin A hydrochloride, lomeguatrib, and chaetocin (2,2',3S,3'S,5aR,5'aR,6,6'-octahydro-3,3'-bis(hydroxymethyl)-2,2'-dimethyl-[10bR,10'bR (11aS,11'aS)-bi-3,11a-epidithio-11aH-pyrazino [1',2': 1,5]pyrrolo[2,3-b]indole]-1,1',4,4'-tetrone); or wherein the supplement is one or more selected from the group consisting of 2-phospho-L-ascorbic acid, B27, laminin, nicotinamide, and N2; or wherein the retinoic acid agonist is one or more selected from the group consisting of TTNPB, phytic acid, and retinoic acid; or wherein the hedgehog inhibitor is one or more selected from the group consisting of cyclopamine, mifepristone, GDC-0449 (vismodegib), XL139 (BMS-833923), IPI926, IPI609 (IPI269609), LDE225, jervine, GANT61, pumorphamine, SAG, SANT-2, tomatidine, SANT74, SANT75, zerumbone, and derivatives thereof; or wherein the MAPK inhibitor is one or more selected from the group consisting of 1-pyridinyl-2-phenylazole, SB 203580, SKF 86002, SKF 86096, SKF 104351, 1-aryl-2-pyridinyl/pyrimidinyl heterocycles, SB 242235, RO-32001195, SX-011, and BIRB-796; or wherein the ALK-5 kinase inhibitor is one or more selected from the group consisting of RepSox (1,5-naphthyridine, 2-[3-(6-methyl-2-pyridinyl)-1H-pyrazol-4-yl]); SB525334 (6-(2-tert-butyl-4-(6-methylpyridin-2-yl)-1H-imidazol-5-yl) quinoxaline); GW788388 (4-(4-(3)-(pyridin-2-yl)-1H-pyrazol-4-yl) pyridin-2-yl)-N-(tetrahydro-2H-pyran-4-yl)benzamide); SD-208 (2-(5-chloro-2-fluorophenyl)-N-(pyridin-4-yl) pteridin-4-amine); Galunisertib (LY2157299, 4-(2-(6-methylpyridin-2-yl)-5,6-dihydro-4H-pyrrolo[1,2-b]pyrazol-3-yl) quinoline-6-carboxamide); EW-7197 (N-(2-fluorophenyl)-5-(6-methyl-2-pyridinyl)-4-[1,2,4] triazolo[1,5-a]pyridin-6-yl-1H-imidazole-2-methanamine); LY2109761 (7-(2-morpholinoethoxy)-4-(2-(pyridin-2-yl)-5,6-dihydro-4H-pyrrolo[1,2-b] pyrazol-3-yl) quinoline); SB505124 (2-(4-(benzo[d][1,3]dioxol-5-yl)-2-tert-butyl-1H-imidazol-5-yl)-6-methylpyridine); LY364947 (quinoline, 4-[3-(2-pyridinyl)-1H-pyrazol-4-yl]); SB431542 (4-(4-(benzo[d][1,3]dioxol-5-yl)-5-(pyridin-2-yl)-1H-imidazol-2-yl)benzamide); K02288 (3)-[(6-amino-5-(3),4,5-trimethoxyphenyl)-3-pyridinyl]phenol]; and LDN-212854 (quinoline, 5-[6-[4-(1-piperazinyl)phenyl] pyrazolo[1,5-a]pyrimidin-3-yl]); or wherein the calcium channel agonist is one or more selected from the group consisting of Bay K-8644, FPL 64179, and CGP28392; or wherein the GLP receptor agonist is one or more selected from the group consisting of Dulaglutide, Exenatide, Semaglutide, Liraglutide, Lixisenatide, and Albiglutide.

6. The method of claim 4, wherein the method for direct reprogramming comprises the following stages:

(1) inducing somatic cells into pancreatic endoderm cells in the presence of a composition comprising a histone methyltransferase inhibitor; activin A, a supplement; and one or more miRNA selected from the group consisting of miR-127 and miR-709;

(2) inducing the endoderm cells into pancreatic endoderm cells in the presence of a composition comprising a retinoic acid agonist, an ALK-5 kinase inhibitor, a hedgehog inhibitor, a supplement; and one or more miRNA selected from the group consisting of miR-127 and miR-709; and (3) culturing the somatic cells in the presence of a composition comprising a MAPK inhibitor, a calcium channel agonist, a GLP receptor agonist, a supplement; and one or more miRNA selected from the group consisting of miR-127 and miR-709.

7. A method for treating diabetes or pancreatic cancer, which comprises administering a composition comprising one or more miRNA selected from the group consisting of miR-127 and miR-709; or pancreatic beta cells, whose direct reprogramming was induced by the method of claim 1, as an active ingredient to a subject in need thereof.

8. The method of claim 7, wherein the diabetes is selected from the group consisting of type 1 diabetes, type 2 diabetes, and gestational diabetes.

9. The method of claim 7, wherein the composition further comprises miR-19b.

10. The method of claim 7, wherein the composition further comprises one or more small molecule selected from the group consisting of a histone methyltransferase inhibitor; a retinoic acid agonist; an ALK-5 kinase inhibitor, a hedgehog inhibitor, a MAPK inhibitor; a calcium channel agonist; a GLP receptor agonist; and a supplement.

11. The method of claim 7, wherein the composition is cellular therapeutic agent.

12. The method of claim 7, wherein the cellular therapeutic agent is prepared by mixing pancreatic beta cells, whose direct reprogramming was induced by the method of claim 1, with one or more selected from the group consisting of pharmaceutically acceptable carriers and excipients.

13. The method of claim 7, wherein the method comprises delivering a composition comprising one or more miRNA selected from the group consisting of miR-127 and miR-709 into the living body to induce direct reprogramming of somatic cells into beta cells in vivo.

* * * * *